United States Patent
Dong et al.

(10) Patent No.: US 7,037,663 B2
(45) Date of Patent: May 2, 2006

(54) HUMAN ZONA PELLUCIDA PROTEIN 3 AND USES THEREOF

(75) Inventors: Ke-Wen Dong, Chesapeake, VA (US); Sergio C. Oehninger, Norfolk, VA (US); William E. Gibbons, Norfolk, VA (US)

(73) Assignee: Eastern Virginia Medical School, Norfolk, VA (US)

( * ) Notice: Subject to any disclaimer, the term of this patent is extended or adjusted under 35 U.S.C. 154(b) by 0 days.

(21) Appl. No.: 09/829,073

(22) Filed: Apr. 9, 2001

(65) Prior Publication Data

US 2002/0028470 A1 Mar. 7, 2002

Related U.S. Application Data

(63) Continuation-in-part of application No. 09/252,828, filed on Feb. 19, 1999.
(60) Provisional application No. 60/075,079, filed on Feb. 19, 1998.

(51) Int. Cl.
*G01N 33/53* (2006.01)

(52) U.S. Cl. ............... 435/7.1; 435/7.21; 435/7.92; 436/501

(58) Field of Classification Search .............. 435/7.1, 435/7.21, 7.92, 4, 5, 6, 7, 240.1, 240.21, 435/69.3, 253.1, 69.1, 240.2, 252, 252.2, 435/252.3, 254.11, 320.1, 325, 235.1; 436/500, 436/501; 530/300, 350, 326; 424/184.1, 204.1, 424/85.8, 88; 536/23.1, 27.1, 23.5, 24.1; 514/2, 13, 14, 21
See application file for complete search history.

(56) References Cited

U.S. PATENT DOCUMENTS

| | | | |
|---|---|---|---|
| 4,399,216 A | | 8/1983 | Axel et al. |
| 4,444,879 A | * | 4/1984 | Foster et al. ................ 435/7 |
| 4,554,101 A | | 11/1985 | Hopp |
| 4,634,665 A | | 1/1987 | Axel et al. |
| 4,861,718 A | | 8/1989 | Hirata et al. |
| 4,889,803 A | | 12/1989 | Revel et al. |
| 4,960,704 A | | 10/1990 | Ingolia et al. |
| 5,034,322 A | | 7/1991 | Rogers et al. |
| 5,179,017 A | | 1/1993 | Axel et al. |
| 5,272,071 A | | 12/1993 | Chappel |
| 5,352,605 A | | 10/1994 | Fraley et al. |
| 5,618,698 A | | 4/1997 | Lin |
| 5,626,846 A | | 5/1997 | Dean |
| 5,641,487 A | | 6/1997 | Dean |
| 5,641,670 A | | 6/1997 | Treco et al. |
| 5,650,321 A | | 7/1997 | Levy |
| 5,672,488 A | | 9/1997 | Dean |
| 5,703,057 A | | 12/1997 | Johnston et al. |
| 5,710,038 A | | 1/1998 | Mes-Masson et al. |
| 5,766,924 A | | 6/1998 | Levy |
| 5,817,793 A | | 10/1998 | Levy |
| 5,821,350 A | | 10/1998 | Huang et al. |
| 5,837,497 A | * | 11/1998 | Harris ....................... 435/693 |
| 5,851,763 A | | 12/1998 | Heym et al. |
| 5,851,796 A | | 12/1998 | Schatz |

(Continued)

FOREIGN PATENT DOCUMENTS

| | | | |
|---|---|---|---|
| EP | 0488470 | | 5/1997 |
| WO | 90/15624 | | 12/1990 |
| WO | WO 92/03548 | * | 3/1992 |
| WO | 93/14786 | | 8/1993 |
| WO | 94/10304 | | 5/1994 |
| WO | WO 94/11019 | * | 5/1994 |
| WO | 94/22472 | | 10/1994 |
| WO | 95/27206 | | 10/1995 |
| WO | 96/05305 | | 2/1996 |
| WO | 96/06113 | | 2/1996 |
| WO | 98/37185 | | 8/1998 |
| WO | 99/34825 | | 7/1999 |
| WO | 99/42581 | | 8/1999 |
| WO | 99/52544 | | 10/1999 |
| WO | 99/64626 | | 12/1999 |
| WO | 99/64627 | | 12/1999 |
| WO | 99/65520 | | 12/1999 |
| WO | 99/65928 | | 12/1999 |

OTHER PUBLICATIONS

Chapman and Barratt, "The role of carbohydrate in sperm–ZP3 adhesion." Molecular human Reproduction, vol. 2, No. 10, pp. 767–774, 1996.*

Chamberlin et al., "Human homolog of the mouse sperm receptor." Proc. Natl. Acad:Sci. USA., vol. 87, pp. 6014–6018, Aug. 1990, Developmental Biology.*

(Continued)

*Primary Examiner*—Long V. Le
*Assistant Examiner*—Lisa V. Cook
(74) *Attorney, Agent, or Firm*—Wilmer Cutler Pickering Hale and Dorr LLP

(57) ABSTRACT

The present invention provides a method to determine sperm activity comprising the steps of: (a) contacting an appropriate concentration of human zona pellucida protein 3 with an appropriate amount of sperm under conditions permitting the formation of a complex between the human zona pellucida protein 3 and the sperm; and (b) determining the complex formed. The invention further provides a method to determine sperm activity comprising the steps of (a) contacting an appropriate concentration of human zona pellucida protein 3 with an appropriate amount of sperm under conditions permitting an acrosome reaction to occur; and (b) determining the extent of the acrosome reaction. Finally, this invention provides a diagnosis kit for sperm activity comprising three (3) compartments with (a) an appropriate amount of human zona pellucida protein 3; (b) the reagents used for establishing the conditions for allowing the binding of sperm; and (c) the reagents used for establishing the conditions for allowing an acrosome reaction.

10 Claims, 12 Drawing Sheets

U.S. PATENT DOCUMENTS

Figure 1:

| | | | |
|---|---|---|---|
| 5,851,817 | A | 12/1998 | Hardy et al. |
| 5,869,053 | A | 2/1999 | Stern et al. |
| 5,888,981 | A | 3/1999 | Bujard et al. |
| 5,891,718 | A | 4/1999 | Hobart et al. |
| 5,916,768 | A | 6/1999 | Dean |
| 5,922,927 | A | 7/1999 | Bujard et al. |
| 5,925,541 | A | 7/1999 | Goldstein et al. |
| 5,962,326 | A | 10/1999 | Shimada et al. |
| 5,968,773 | A | 10/1999 | Heddle et al. |
| 5,976,545 | A | 11/1999 | Harris et al. |
| 5,981,228 | A | 11/1999 | Harris et al. |
| 5,989,550 | A | 11/1999 | Harris et al. |
| 6,001,599 | A | 12/1999 | Harris et al. |
| 6,027,727 | A | 2/2000 | Harris et al. |
| 6,132,952 | A | 10/2000 | Cohen et al. |
| 6,264,953 | B1 | 7/2001 | Dunbar |
| 2002/0172892 | A1 | 11/2002 | Dong et al. |
| 2003/0148930 | A1 | 8/2003 | Chi et al. |

OTHER PUBLICATIONS

Ozgur et al., "Direct evidence for the involvement of carbohydrate sequences in humna sperm–zona pellucida binding.", Molecular Human Reproduction, vol. 4, No. 4, 1998, pp. 318–324.*

Van Duin et al., "Recombinant human zona pellucida protein ZP3 by chinese hamster ovary cells induces the human sperm acrosome reaction and promotes sperm–egg fusion." Biology of Reproduction, vol. 51, pp. 607–617, 1994.*

Edward T. Maggio, Enzyme–Immunoassay, pp. 186–187, May 14, 1987.*

Bleil, Jeffrey A. et al. 1980, "Structure and Function of the Zona Pellucida: Identification and Characterization of the Proteins of the Mouse Oocyte's Zona Pellucida." *Dev. Bio.* vol. 76, pp. 185–202.

Barbosa, James A. 1987. "Site–Directed Mutagenesis of Class I HLA Genes: Role of Glycosylation in Surface Expression and Functional Recognition." *J. Exp. Med.* vol. 166, pp. 1329–50.

Burkman, Lani J. et al. 1988. "The Hemizona Assay (HZA): Development of a Diagnositic Test for the Binding of Human Spermatozoa to the Human Hemizona Pullucida to Predict Fertilization Potential." *Fertility and Sterility.* vol. 49, pp. 688–693.

Kinloch, Ross A. et al. 1988. "Primary Structure of the Mouse Sperm Receptor Polypeptide Determined by Genomic Cloning." *Proc. Natl. Sci.* vol. 85, pp. 6409–6413.

Mansour, Suzanne L. 1988. Disruption of the Proto–Oncogene Int–2 in Mouse Embryos–derived Stem Cells: A General Strategy for Targeting Mutations to Non–Selectable Genes. *Nature.* vol. 336, pp. 348–349.

Saling, Patricia. 1989. "Mammalian Sperm Interaction with Extracellular Matrices of the Egg." *Oxford Reviews of Reproductive Biology.* vol. 11, pp. 339–388.

Chamberlin et al. Aug. 1990. "Human Homolog of the Mouse Sperm Receptor." *Proceedings of the National Academy of Sciences of USA.* vol. 87, pp. 6014–6018, XP–00210857.

Saling, Patricia. 1991. "How the Egg Regulates Sperm Function During Gamete Interaction: Facts and Fantasies." *Biology of Reproduction.* vol. 44, pp. 246–251.

Beebe, Stephen J. et al. 1992, Recombinant Mouse ZP3 Inhibits Sperm Binding and Induces the Acrosome Reaction. *Dev. Biol.* vol. 151, pp. 48–54.

Oehninger, S. et al. 1992. "Hermizona Assay and Its Impact on the Identification and Treatment of Human Sperm Dysfunctions." *Andrologia.* vol. 24, pp. 307–321.

Kinloch et al. Jan. 1995. "Mapping the Mouse ZP3 Combining Site for Sperm by Exon Swapping and Site–Directed Mutagenesis." *Proceedings of the National Academy of Sciences of USA.* vol. 92, pp. 263–267, XP–002108572.

Clark et al. 1996. "Role for Glycoconjugates in Cellular Communication in the Human Reproductive System." *Molecular Human Reproduction.* vol. 2, No. 7, pp. 513–517.

Clark, Gary F. et al. 1996. "A Role for Glycoconjugates in Human Development: The Human Feto–embryonic Defense System Hypothesis." *Human Reproduction.* vol. 11, pp. 467–473.

Bagavant et al. Mar. 1997. "Immunogenicity and Contraceptive Potential of a Zona Pellucida 3 Peptide Vaccine." *Biology of Reproduction.* vol. 56, No. 3, pp. 764–770, XP–002108575.

Chapman et al. 1997. "2. Sperm–zona Interaction and Recombinant DNA Technology." *Molecular Human Reproduction.* vol. 3, No. 8, pp. 646–650.

Hansen et al. 1997. "O–GLYCBASE Version 2.0: a Revised Database of O–glycosylated Proteins." *Nucleic Acids Research.* vol. 25, No. 1, pp. 178–282.

Patankar et al. 1997. "Expression of Glycans Linked to Natural Killer Cell Inhibition of the Human Zona Pellucida." *Molecular Human Reproduction.* vol. 3, No. 6, pp. 501–505.

Chen et al. May 1998. "Inactivation of the Mouse Sperm Receptor, mZP3, by Site–directed Mutagenesis of Individual Serine Residues Located at the Combining Site for Sperm." *Proc. Natl. Acad. Sci. USA.* vol. 95, pp. 6193–6197.

Hansen et al. 1998. "NetOglyc: Prediction of Mucin Type O–glycosylation Sites Based on Sequence Context and Surface Accessibility." *Glycoconjugate Journal.* pp. 115–130.

Chirgwin, John M., Alan E. Przybla, Raymond J. MacDonald, and William J. Rutter. 1979. "Isolation of Biologically Active Ribonucleic Acid from Sources Enriched in Ribonuclease." *Biochemistry.* vol. 18, No. 24, pp. 5294–5299.

Bleil, Jeffrey D. and Paul M. Wassarman. Jul. 1980. "Mammalian Sperm–Egg Interaction: Identification of a Glycoprotein in Mouse Egg Zonae Pellucidae Possessing Receptor Activity for Sperm." *Cell.* vol. 20, pp. 873–882.

Dunbar, Bonnie S., Cecilia Liu, and David W. Sammons. 1981. "Identification of the Three Major Proteins of Porcine and Rabbit Zonae Pellucidae by High Resolution Two–Dimensional Gel Electrophoresis: Comparison with Serum, Follicular Fluid, and Ovairan Cell Proteins." *Biology of Reproduction.* vol. 24, pp. 1111–1124.

McIlhinney, R. A. J. and Shashikant Patel. Mar. 1983. "Characterization of the Fibronectin Synthesized by Human Germ Cell Tumors.," *Cancer Research.* vol. 43, pp. 1282–1288.

Florman, Harvey M. and Paul M. Wassarman. May 1985. "O–Linked Oligosaccharides of Mouse Egg ZP3 Account for Its Sperm Receptor Activity." *Cell.* vol. 41, pp. 313–324.

Fukuda, Michiko N., Anne Dell, Jane E. Oates, and Minoru Fukuda. Jun. 1985. "Embryonal Lactosaminoglycan: The Structure of Branched Lactosaminoglycans with Novel Disialosyl (Sialyl alpha2→9 Sialyl) Terminals Isolated from PA1 Human Embryonal Carcinoma Cells." *The Journal of Biological Chemistry.* Vo. 260, No. 11, pp. 6623–6631.

Cross, Nicholas L., Patricio Morales, James W. Overstreet, and Frederick W. Hanson. May 1986. "Two Simple Methods for Detecting Acrosome–Reacted Human Sperm." *Gamete Research.* vol. 15, pp. 213–226.

Ringuette, Maurice J., Donna A. Sobieski, Steven M. Chamow, and Jurrien Dean. Jun. 1986. "Oocyte–Specific Gene Expression: Molecular Characterization of a cDNA Coding for ZP–3, the Sperm Receptor of the Mouse Zona Pellucida." *Proc. Natl. Acad. Sci. USA.* vol. 83, pp. 4341–4345.

Burkman, Lani J., Charles C. Coddington, Daniel R. Franke, Thinus F. Kruger, Zev Rosenwaks, and Gary D. Hodgen. Apr. 1988. "The Hemizona Assay (HZA): Development of a Diagnositc Test for the Binding of Human Spermatozoa to the Human Hemizona Pellucida to Predict Fertilization Potential." *Fertility and Sterility.* vol. 49, No. 4, pp. 688–697.

Shabanowitz, R. B. and M. G. O'Rand. 1988. "Characterization of the Human Zona Pellucida from Fertilized and Unfertilized Eggs." *J. Reprod. Fert.* vol. 82, pp. 151–161.

Timmons, T. M. and B. S. Dunbar. 1988. "Antigens of Mammalian Zona Pellucida." *Perpectives in Immunoreproduction: Conception and Contraception.* New York: Hemisphere Publishing Co. pp. 242–260.

Wassarman, Paul M. 1988. "Zona Pellucida Glycoproteins." *Ann. Rev. Biochem.* vol. 57, pp. 415–442.

Saling, Patricia M. 1989. "Mammalian Sperm Interaction with Extracellular Matrices of the Egg." *Oxf. Rev. Reprod. Biol.* vol. 11, pp. 339–388.

Sambrook J., E.F. Fritsch, and T. Maniatis. 1989. *Molecular Cloning: A Laboratory Manual.* $2^{nd}$ Edition. Cold Spring Harbor Laboratory Press. pp. 16.32–16.37.

Oehninger, Sergio, Anibal Acosta, and Gary D. Hodgen. Jan. 1990. "Antagonistic and Agonistic Properties of Saccharide Moieties in the Hemizona Assay." *Fertility and Sterility.* vol. 53, No. 1, pp. 143–149.

Furukawa, Tatsuhiko, Masayuki Ozawa, Ruo–Pan Huang, and Takashi Muramatsu. Mar. 1990. "A Heparin Binding Protein Whose Expression Increases During Differentiation of Embryonal Carcinoma Cells to Parietal Endoderm Cells: cDNA Cloning and Sequence Analysis." *J. Biochem.* vol. 108, No. 2, pp. 297–302.

Liang, Li–Fang, Steven M. Chamow, and Jurrien Dean. Apr. 1990. "Oocyte–Specific Expression of Mouse Zp–2:Developmental Regulation of the Zona Pellucida Genes." *Molecular and Cellular Biology.* vol. 10, No. 4, pp. 1507–1515.

Kinloch, Ross A., Betina Ruiz–Seiler, and Paul. M. Wassarman. Aug. 1990. "Genomic Organization and Polypeptide Primary Structure of Zona Pellucida Glycoprotein hZP3, the Hamster Sperm Receptor." *Developmental Biology.* vol. 142, pp. 414–421.

Wassarman, Paul M. 1990. "Profile of a Mammalian Sperm Receptor." *Development.* vol. 108, pp. 1–17.

Wassarman, P. M. 1990. "Regulation of Mammalian Fertilization by Zona Pellucida Glycoproteins." *J. Reprod. Fert., Suppl.* vol. 42, pp. 79–87.

1991. "Errata." *Developmental Biology.* vol. 145, pp. 203–204.

Saling, Patricia M. 1991. "How the Egg Regulates Sperm Function During Gamete Interaction: Facts and Fantasies." *Biology of Reproduction.* vol. 44, pp. 246–251.

Beebe, Stephen J., Lisette Leyton, Deborah Burks, Motoharu Ishikawa, Tom Fuerst, Jurrien Dean, and Patricia Saling. Jan. 1992. "Recombinant Mouse ZP3 Inhibits Sperm Binding and Induces the Acrosome Reaction." *Developmental Biology.* vol. 151, pp. 48–54.

Thillai–Koothan, P., Marcel Van Diun, and R. John Aitken. May 1993. "Cloning, Sequencing and Oocyte–Specific Expression of the Marmoset Sperm Receptor Protein, ZP3." *Zygote.* vol. 1, pp. 93–101.

Lee, Vaughan H., Eric Schwoebel, Sarvamangala Prasad, Peter Cheung, Therese M. Timmons, Richard Cook, and Bonnie S. Dunbar. Jun. 1993. "Identification and Structural Characterization of the 75–kDa Rabbit Zona Pellucida Protein." *The Journal of Biology Chemistry.* vol. 268, No. 17, pp. 12412–12417.

Liang, Li–Fang and Jurrien Dean. 1993. "Conservation of Mammalian Secondary Sperm Receptor Genes Enables the Promoter of the Human Gene to Function in Mouse Oocytes." *Developmental Biology.* vol. 156, pp. 399–408.

Varki, Ajit. 1993. "Biological Roles of Oligosaccharides: All of the Theories Are Correct." *Glycobiology.* vol. 3, No. 2, pp. 97–130.

Barratt, C.L.R., A. Whitmarsh, D.P. Hornby, S. Clements, I.D. Cooke, and H.D.M. Moore. 1994. "Glycosylation of Human Recombinant ZP3 Is Necessary to Induce the Human Acrosome Reaction" (Abstract No. 33). *Hum. Reprod.* vol. 9 (Suppl.).

Dunbar, B. S., S. Avery, V. Lee, S. Prasad, D. Schwahn, E. Schwoebel, S. Skinner, and B. Wilkins. 1994. "The Mammalian Zona Pellucida: Its Biochemistry, Immunochemistry, Molecular Biology, and Development Expression." *Reprod. Fertil. Dev.* vol. 6, pp. 331–347.

Hinsch, Klaus–Dieter, Elvira Hinsch, Burkhard Meinecke, Edda Töpfer–Petersen, Susanne Pfisterer, and Wolf–Bernhard Schill. 1994. "Identification of Mouse ZP3 Protein in Mammalian Oocytes with Antisera Against Synthetic ZP3 Peptides." *Biology of Reproduction.* vol. 51, pp. 193–204.

Varki, Ajit. 1994. "[2] Metabolic Radiolabeling of Glycoconjugates." *Methods in Enzymology.* vol. 230, pp. 16–32.

Oehninger, Sergio, Charles C. Coddington, Gary D. Hodgen, and Markku Seppala, Feb. 1995. "Factors Affecting Fertilization: Endometrial Placental Protein 14 Reduces the Capacity of Human Spermatozoa to Bind to the Human Zona Pellucida." *Fertility and Sterility.* vol. 63, No. 2, pp. 377–383.

Burks, D. J., R. Carballada, H. D. M. Moore, and P. M. Saling. Jul. 1995. "Interaction of a Tyrosine Kinase from Human Sperm with the Zona Pellucida at Fertilization." *Science.* vol. 269, pp. 83–86.

Barratt, Christopher L.R. and David P. Hornby. "Induction of the Human Acrosome Reactions by rhuZP3." 1995. *Human Sperm Acrosome Reaction.* Colloque INSERM/John Libbey Eurotext Ltd. vol. 236, pp. 105–122.

Lust, J.A., D.F. Jelinek, K.A. Donovan, L. A. Frederick, B.K. Huntley, J.K. Braaten, and N.J. Maihle, 1995. "Sequence, Expression and Function of an mRNA Encoding a Soluble Form of the Human Interleukin–6 Receptor (sIL–6R)." *Curr. Top. Microbiol. Immunol.* vol. 194, pp. 199–206.

Whitmarsh, A.J., M.J. Woolnough, H.D.M. Moore, D.P. Hornby, and C.L.R. Barratt. 1996. "Biological Activity of Recombinant Human ZP3 Produced in vitro: Potential for a Sperm Function Test." *Molecular Human Reproduction.* vol. 2, No. 12, pp. 911–919.

Franken, Daniel R., Patricio J. Morales, and Ursula F. Habenicht. Dec. 1996. "Inhibition of G Protein in Human Sperm and Its Influence on Acrosome Reaction and Zona Pellucida Binding." *Fertility and Sterility.* vol. 66, No. 6, pp. 1009–1011.

Brewis, I.A., R. Clayton, C.L.R. Barratt, D.P.J. Hornby, and H.D.M. Moore. 1996. "Recombinant Human Zona Pellucida Glycoprotein 3 Induces Calcium Influx and Acrosome Reaction in Human Spermatozoa." *Molecular Human Reproduction.* vol. 2, No. 8, pp. 583–589.

Chapman, Neil R. and Christopher L.R. Barrat. 1996. "The Role of Carbohydrate in Sperm–ZP3 Adhesion." *Molecular Human Reproduction.* vol. 2, No. 10, pp. 767–774.

Prasad, Sarvamangala V., Brendan Wilkins. Sheri M. Skinner, and Bonnie S. Dunbar. 1996. "Evaluating Zona Pellucida Structure and Function Using Antibodies to Rabbit 55 kDa ZP Protein Expressed in Baculovirus Expression System." *Molecular Reproduction and Development.* vol. 43, pp. 519–529.

Dong, Ke Wen, Ting Fung Chi, Yu Wen Juan, Chih Wei Chen, Zhiyong Lin, Xiao–Qin Xiang, Mary Mahoney, William E. Gibbons, and Sergio Oehninger. Apr. 2001. "Characterization of the Biologic Activities of a Recombinant Human Zona Pellucida Protein 3 Expressed in Human Ovarian Teratocarcinoma (PA–1) Cells." *Am. J. Obstet. Gynecol.* pp. 835–844.

Harrison R. G. May 25–27,1960. "Proceedings of the Society for the Study of Fertility,"*Annual Conference,* London.

Hartmann, John F. et al. Oct. 1972. "Early Contact Interactions Between Mammalian Gametes *In Vitro:*Evidence That the Vitellus Influences Adherence Between Sperm and Zona Pellucida."*Proc. Nat. Acad. Sci.*USA. vol. 69, No. 10, pp. 2767–2769.

O'Farrell, Patrick H. May 25, 1975. "High Resolution Two–Dimensional Electrophoresis of Proteins."*The Journal of Biological Chemistry.* vol. 250, No. 10, pp. 4007–4021.

Russell, Lonnie et al. Jul. 1979. "Morphologic Characteristics of the Chemically Induced Acrosome Reaction in Human Spermatozoa. "*Fertility and Sterlity.* vol. 32, No. 1, pp. 87–92.

Saling, Patricia M. et al. 1979. "An Ultrastructural Study of Epididymal Mouse Spermatozoa Binding to Zonae Pellucidae in Vitro: Sequential Relationship to the Acrosome Reaction."*J. Exp. Zool.* vol. 209, pp. 229–238.

Hook, Ernest B. Sep. 1981. "Rates of Chromosome Abnormalites at Different Maternal Ages."*Obstetrics and Gynecology.* vol. 58, No. 3, pp. 282–285.

Koehler, James K. 1981. "Surface Alterations During the Capacitation of Mammalian Spermatozoa."*American Journal of Primatology.* vol. 1, pp. 131–141.

Yanagimachi, R. 1981. "Mechanisms of fertilization in mammals", In Mastroianni L Jr and Biggers JD (eds): *Fertilization and Embryonic Development In Vitro.* New York, Plenum Press, pp. 81–182.

Yanagimachi, Ryuzo et al. 1981. "Sperm Autoantigens and Fertilization: II. Effects of Anti–Guinea Pig Sperm Autoantibodies on Sperm–Ovum Interactions."*Biology of Reproduction.* vol. 24, pp. 512–518.

Ficsor, Gyula et al. Apr. 1983. "Gelatin–Substrate Film Technique for Detection of Acrosin in Single Mammalian Sperm."*Fertilty and Sterility.* vol. 39, No. 4, pp. 548–552.

Mack, S. et al. 1983. "Acrosomal Enzymes of Human Spermatozoa Before and After In Vitro Capacitation."*Biology of Reproduction.* vol. 58, pp. 1032–1042.

Hyne, R. V. et al. 1984. "Sodium Requirements for Capacitation and Membranes Fusion During the Guinea–Pig Sperm Acrosome Reaction."*J. Reprod. Fert.* vol. 70, pp. 83–94.

Bleil, Jeffery D. and Paul M. Wasserman. Apr. 1986. "Autoadiographic Visuallization of the Mouse Egg's Sperm Receptor Bound to Sperm. "*The Journal of Cell Biology.* vol. 102, pp. 1363–1371.

Menken, Jane et al. Sep. 26, 1986. "Age and Infertility." *Science.* vol. 233, pp. 1389–1394.

Fournier–Delpech, Suzanne and Michel Courot. "Sperm–Zona Pellucida Binding Activity."*Oxford Reviews of Reproductive Biology.* vol. 9, pp. 294–300.

Lee, Michael A. et al. Oct. 1987. "Capacitation and Acrosome Reactions in Human Spermatozoa Monitored by a Chlortetracycline Fluorescene Assay."*Fertility and Sterility.* vol. 48, No. 4, pp. 649–658.

Timmons, T. M. et al. 1987. "Use of Specific Monoclonal and Polyclonal Antibodies to define Distinct Antigens of the Porcine Zonae Pellucidae."*Biology of Reproduction.* vol. 36, pp. 1275–1287.

Bleil, Jeffrey D. and Paul M. Wassarman, Sep. 1988. "Galactose at the Nonreducing Terminus of O–Linked Oligosaccharides of Mouse Egg Zona Pellucida Glycoprotein ZP3 Is Essential for the Glycoprotein's Sperm Receptor Activity."*Proc. Natl. Acad. Sci.* USA. vol. 85, pp. 6778–6782.

Ward, Cynthia R. and Bayard T, Storey. 1984. "Determination of the Time Course of Capacitation in Mouse Spermatozoa Using a Chlortetracycline Flourescence Assay."*Development Biology.*vol. 104. pp. 287–296.

Conover, JC and Gwatkin, RB. Jul. 1988. "Fertilization of zona–drilled mouse oocytes treated with a monoclonal antibody to the zona glycoprotein, ZP3."*J. Exp. Zool.*vol. 247, No. 1, pp. 113–8.

Shabanowitz, RB and O'Rand, 1988. "Molecular changes in the human zona pellucida associated with fertilization and human sperm–zona interactions."*Ann. N.Y. Acad. Sci.*vol. 541, pp. 621–32.

Cross, Nicholas L. et al. 1988. "Induction of Acrosome Reactions by the Human Zona Pellucida."*Biology of Reproduction.*vol. 38, pp. 235–244.

Liu, De Yi et al. Nov. 1988. "A Human Sperm–Zona Pellucida Binding Test Using Oocytes That Failed to Fertilize In Vitro."*Fertility and Sterility.*vol. 50, No. 5, pp. 782–788.

Macek, Mary Beth and Barry D. Shur. 1988. "Protein–Carbohydrate Complementarity in Mammalian Gamete Recongnition."*Gamette Research.*vol. 20, pp. 93–109.

Kennedy, W.P. et al. May/Jun. 1989. "A Simple, Clincal Assay to Evaluate the Acrosin Activity of Human Spermatozoa."*Journal of Andrology.*vol. 10, No. 3, pp. 221–231.

Leyton, Lisette and Patricia Saling. Jun. 1989. "Evidence That Aggregation of Mouse Sperm Receptors by ZP3 Triggers the Acrosome Reaction."*The Journal of Cell Biology.*vol. 108, pp. 2163–2168.

Jones, R. 1990. "Identification and Functions of Mammalian Sperm–Egg Recognition Molecules During Fertilization."*J. Reprod. Fert., Suppl.*vol. 42, pp. 89–105.

Von–Bernhardt, R. et al. Jan.–Feb. 1990. "Round–headed spermatozoa: a model to study the role of the acrosome in early events of gamete interaction."*Andrologia.*vol. 22, No. 1, pp. 12–20.

Shabanwitz, RB. Aug. 1990. "Mouse antibodies to human zona pellucida: evidence that human ZP3 is strongly immunogenic and contains two distinct isomer chains."*Biol. Reprod.* vol. 43, No. 2, pp. 260–70.

Kopf, G. S. 1990. "Zona Pellucida–Mediated Signal Transuction in Mammalian Spermatozoa."*J. Reprod. Fert., Suppl.* vol. 42, pp. 33–49.

Topfer–Petersen E. et al. 1990. "Cell biology of acrosomal proteins."*Andrologia;*vol. 22, No. 1, pp. 110–21.

Naz, RK et al. May 1991. "Role of membrane phosphotyrosine proteins in human spermatozoal function."*J. Cell. Sci.* vol. 99, No. 1, pp. 157–65.

Koyama, K. et al. Nov. 1991. "Blocking of Human sperm–zona interaction by monoclonal antibodies to a glycoprotein family (ZP4) of porcine zona pelluica."*Biol. Reprod.*vol. 45, No. 5, pp. 727–35.

Yurewicz, EC et al. Oct. 1991. "Isolation, composition, and biological activity of sugar chains of porcine oocyte zona pellucida 55K glycoproteins."*Mol. Reprod. Dev.*vol. 30, No. 2, pp. 126–34.

Millar, SE et al. Dec. 1991. "Oocyte–specific bind a conserved upstream sequence required for mouse zona pellucida promoter activity."*Mol. Cell. Biol.*vol. 11, No. 12, pp. 6197–204.

Keenan, JA et al. Jan. 1991. "Endocrine response in rabbits immunized with native versus deglycosylated porcine zona pellucida antigens."*Biol. Reprod.*vol. 44, No. 1, pp. 150–6.

Naz, RK et al. May 1991. "Human spermatozoal FA–1 binds with ZP3 of porcine zona pellucida."*J. Reprod. Immunol.* vol. 20, No. 1, pp. 43–58.

Hasegawa, A. Feb. 1991. "Isolation of four major glycoprotein families (ZP1, ZP2, ZP3, ZP4) of porcine zona pellucida and characterization of antisera raised to each glycoprotein family."*Nippon Sanka Fujinka Gakkni Zasshi.*vol. 43, No. 2, pp. 221–6.

Oehninger, Sergio et al. Jan. 1991. "Nature of the Inhibitory Effect of Complex Saccharide Moieties on the Tight Binding of Human Spermatozoa to the Human Zona Pellucida," *Fertility and Sterility.* vol. 55, No. 1, pp. 165–169.

Schwoebel, Eric et al, Apr. 15, 1991. "Isolation and Characterization of a Full–Length cDNA Encoding the 55–kDa Rabbit Zona Pellucida Protein."*The Journal of Biological Chemistry.*vol. 266, No. 11, pp. 7214–7219.

Oehninger, Sergio et al. May 1991. "Recurrent Failure of In Vitro Fertilization: Role of the Hemizona Assay in the Sequential Diagnosis of Specific Sperm–Oocyte Defects." *Am. J. Obstet. Gynecol.* vol. 164, pp. 1210–1215.

Aarons, David et al. 1991. "Acrosome Reaction Induced by Immunoaggregation of a Proteinase Inhibitor Bound to the Murine Sperm Head."*Molecular Reproduction and Development.*vol. 30, pp. 258–264.

Macek, Mary Beth et al. 1991. "Aggregation of β–1, 4–Galactosyltransferase on Mouse Sperm Induces the Acrosome Reaction."*Development Biology.*vol. 147, pp. 440–444.

Mortillo, Steven and Paul M. Wassarman. 1991. "Differential Binding of Gold–Labeled Zona Pellucida Glycoproteins mZP2 and mZP3 to Mouse Sperm Membrane Compartments."*Development.* vol. 113, pp. 141–149.

Wassarman, Paul M. and Steven Mortillo. 1991. "Structure of the Mouse Egg Extracellular Coat, the Zona Pellucida." *International Review of Cytology.* vol. 130, pp. 85–87.

Dean, Jurrien. Apr. 1992. Apr. 1992. "Biology of Mammalian Fertilization: Role of the Zona Pellucida."*The Journal of Clinical Investigation, Inc.* vol. 89, pp. 1055–1059.

Oehninger, Sergio. 1992. "Diagnostic Significance of Sperm–Zona Pellucida."*Reproductive Medicine Review.* vol. 1, pp. 57–81.

Prasher, Douglas C. et al. 1992. "Primary Structure of the *Aequorea Victoria* Green–Fluorescent Protein."*Gene.* vol. 111, pp. 229–233.

Rosiere, Thomas K. and Paul M. Wassarman. 1992. "Identification of a Region of Mouse Zona Pellucida Glycoprotein mZP3 That Possesses Sperm Receptor Activity."*Developmental Biology.* vol. 154, pp. 309–317.

Salzberger, Z. et al. 1992. "Loss of Acid Phosphatase from Rat Spermatozoa as a Method for Assessing the Acrosome Reaction."*Andrologia.* vol. 24, pp. 155–159.

Rhim, SH et al. Jan. 1992. "Autoimmune disease of the ovary induced by a ZP3 peptide from the mouse zona pellucida."*J. Clin. Invest.* vol. 89, No. 1, pp. 28–35.

Yurewicz,, EC et al. Oct. 1992. "Porcine oocyte zona pellucida M(r) 55,000 glycoproteins: identification of O–glycosylated domains."*Mol. Reprod. Dev.* vol. 33, No. 2, pp. 182–8.

Paterson, M. et al. Apr. 1992. "Analysis of the contraceptive potential of antibodies against native and deglycosylated porcine ZP3 in vivo and in vitro."*Biol. Reprod.* vol. 46, No. 4, pp. 523–34.

Tulsiani, DR et al. Jan. 1992. "Evidence for the presence of high–mannose/hybrid oligosaccharide chain(s) on the mouse ZP2 and ZP3."*Biol. Reprod.* vol. 46, No. 1, pp. 93–100.

Van Duin et al. 1992. "Cloning and Characterization of the Human Sperm Receptor Ligand ZP3: Evidence of a Second Polamorphic Allele with Different Frequency in the Causasian and the Japanese Populations."*Genomics.* vol. 14, No. 4, pp. 1064–1070. XP–002108574.

Bagavant, H. et al. Dec. 1993. "Block in porcine gamete interaction by polyclonal antibodies to a pig ZP3 beta fragment having partial sequence homology to human ZP3."*J. Reprod. Immunol.*vol. 25, No. 3, pp. 277–83.

Toner, James P. and Jill Taylor Flood. Jun. 1993. "Fertility After the Age of 40."*Perimenopausal Health Care.*vol. 20, No. pp. 261–272.

Patankar, Manish S. et al. Oct. 15, 1993. "A Revised Structure for Fucoidan May Explain Some its Biological Activities."*The Journal of Biological Chemistry.*vol. 268, No. 29, pp. 21770–21776.

Oehninger, Sergio et al. 1993. "The Specificity of Human Spermatozoa/Zona Pellucida Interaction Under Hemizona Assay Conditions."*Molecular Reproduction and Development.*vol. 35, pp. 57–61.

Yurewicz, Edward C. et al. 1993. "Porcine Zona Pellucida ZP3αGlycoprotein Mediates Binding of the Biotin–Labeled $M_r$ 55,000 Family (ZP3) to Boar Sperm Membrane Vesicles." *Molecular Reproduction and Development.*vol. 36, pp. 382–389.

Yurewicz, EC et al. May 1993. "Generation and Characterization of site–directed antisera against an amino–terminal segment of a sskDa sperm adhesive glycoprotein from zona pellucida of pig oocytes."*J. Reprod. Fertil.*vol. 98, No. 1, pp. 147–52.

Yurewicz, EC et al. Aug. 1993. "Nucleotide sequence of cDNA encoding ZP3 alpha, a sperm–binding glycoprotein from zona pellucida of pig oocyte."*Biochem. Biophys. Acta.* vol. 1174, No. 2, pp. 211–4.

Van Duin, M. et al. 1993. "The human gene for zona pellucida glycoprotein ZP3 and a second polymorphic locus are located on chromosome 7"*Cytogenet. Cell. Genet.*vol. 63, No. 2, pp. 111–3.

Chalfie, M. et al. Feb. 1994. "Green fluorescent protein as a marker for gene expression."*Science.*vol. 263, No. 5148, pp. 802–5.

Wang, Shengxian and Tulle Hazelrigg. Jun. 2, 1994. "Implications for *bcd*mRNA Localization from Spatial Distribution of *exu*Protein in *Drosophila Oogenesis.*"*Nature.*vol. 369, pp. 400–403.

Arts, Eugene G. J. M. et al. Nov. 1994. "A New Method to Detect Acrosome–Reacted Spermatozoa Using Biotinylated Soybean Trypsin Inhibitor."*Fertility and Sterility.*vol. 62, No. 5, pp. 1044–1055.

Bielfeld, Peter et al. Dec. 1994. "Are Capacitation or Calcium Ion Influx Required for the Human Sperm Acrosome Reaction?"*Fertility and Sterility.*vol. 62, No. 6, pp. 1255–1261.

Flach, Jean et al. Dec. 1994. "A Yeast RNA–Binding Protein Shuttles Between the Nucleus and the Cytoplasm."*Molecular and Cellular Biology.* vol. 14, No. 12, pp. 8399–8407.

Inouye, Satoshi and Frederick I. Tsuji. 1994. "Evidence for Redox Forms of the *Aequorea* Green Flourescent Protein." *FEBS Letters.*vol. 351, pp. 211–214.

Naz, RK et al. Dec. 1994. "Molecular identities of human sperm proteins that bind human zona pellucida: nature of sperm–zona interaction, tyrosine kinase activity, and the involvement of FA–1."*Mol. Reprod. Dev.*vol. 39, No. 4, pp. 397–408.

Bagavant, H. et al. Sep. 1994. "Antifertility effects of porcine zona pellucida–3 immunization using permissible adjuvants in female bonnet monkeys (Macaca radiato): reversibility, effect on follicular development and hormonal profiles."*J. Reprod. Fert.,*vol. 102, No. 1, pp. 17–25.

Hinsch, KD et al. Oct. 1994. "Anti–ZP3 antibodies binding to the human zona pellucida: effect of oocyte–storage conditions."*Am. J. Reprod. Immunol.*vol. 32, No. 3, pp. 146–51.

Wydner, KS et al. Sep. 1994. "Use of an intron polymorphism to localize the tropoelastin gene to mouse chromosome 5 in a region of linkage conservation with human chromosome 7."*Genomics.*vol. 23, No. 1, pp. 125–31.

Cui, KH et al. Jan. 1994. "Sex determination of preimplantation embryos by human testis–determining gene amplification."*Lancet.*vol. 343, No. 8889, pp. 79–82.

Crozet, N. May 1994. "Acrosome reaction and fertilization." *Contracept. Fertil. Sex.*vol. 22, No. 5, pp. 328–30.

Marshall, John et al. Feb. 1995. "The Jellyfish Green Flourescent Protein: A New Tool for Studying Ion Channel Expression and Function."*Neuron.*vol. 14, pp. 211–215.

Henkel, Ralf et al. May/Jun. 1995. "Acrosin Activity of Human Spermatozoa by Means of a Simple Gelatinolytic Technique: A Method Useful for IVF."*Journal of Andrology.*vol. 16, No. 3, pp. 272–277.

Epifano, O. et al. Nov. 1995. "Mouse ZP1 encodes a zona pellucida protein homologous to egg envelope proteins in mammals and fish."*J. Biol. Chem.*vol. 270, No. 45, pp. 27254–8.

Lou, YH et al. Oct. 1995. "Altered target organ. A mechanism of postrecovery resistance to murine autoimmune oophoritis."*J. Immunol.*vol. 155, No. 7, pp. 3667–73.

Aitken, RJ et al. May 1995. "Redox regulation of tyrosine phosphorylation in human spermatazoa and its role in the control of human sperm function."*J. Cell. Sci.*vol. 108, No. 108, No. 5, pp. 2017–25.

Nata, K. et al. Jun. 1995. "The structure of the Aplysis kurodai gene encoding ADP–ribosyl cyclase, a second–messenger enzyme."*Gene.*vol. 158, No. 2, pp. 213–8.

Perry, Raquel L. et al. Jul. 1995. "A Time Course Study of Capacitation and the Acrosome Reaction in Human Spermatozoa Using a Revised Chlortetracycline Pattern Classification."*Fertility and Sterility.*vol. 64, No. 1, pp. 150–159.

Dell, Anne et al. Oct. 13, 1995. "Structural Analysis of the Oligosaccharides Derived from Glycodelin, a Human Glycoprotein with Potent Immunosuppressive and Contraceptive Activtites."*The Journal of Biological Chemistry.*vol. 270, No. 41, pp. 24116–24126.

Kolluri, SK et al. 1995. "Nucleotide sequence of cDNA encoding bonnet monkey (Macaca radiata) zona pellucida glycoprotein–ZP3."*Reprod. Fert. Dev.*vol. 7, No. 5, pp. 1209–12.

MacKenna, A. 1995. "Contribution of the Male Factor to Unexplained Infertility: A Review."*International Journal of Andrology.*vol. 18, Suppl. 1, pp. 58–61.

Stearns, Tim. 1995. "The Green Revolution: Green Flourescent Protein Allows Gene Expression and Protein Localization to be Observed in Living Cells."*Current Biology.*vol. 5, No. 3, pp. 262–264.

Wassarman, Paul M. and Eveline S. Litscher. 1995. "Sperm—Egg Recognition Mechanisms in Mammals."*Current Topics in Development Biology.*vol. 30, pp. 1–19.

Cheng, Feng–Pang et al. Nov./Dec. 1996. "Use of Peanut Agglutinin to Assess the Acrosomal Status and the Zona Pellucida–Induced Acrosome Reaction in Stallion Spermatozoa."*Journal of Andrology.*vol. 17, No. 6, pp. 674–682.

Mooris, Howard R. et al. Dec. 13, 1996. "Gender–Specific Glycosylation of Human Glycodelin Affects Its Contraceptive Activity."*The Journal of Biological Chemistry.*vol. 271, No. 50, pp. 32159–32167.

Barros, C. et al. 1996. "Early Steps of Sperm–Egg Interactions During Mammalian Fertilization."*Cell Biology International.*vol. 20, No. 1, pp. 33–39.

Bruch, J et al. 1996. "Mapping of Type I loci from human chromosome 7 reveals segments of conserved synteny on pig chromosomes 3, 9, and 18."*Cytogenet. Cell. Genet.*vol. 73, No. 3, pp. 164–7.

Liu, De Yi and H.W. Gordon Baker. 1996. "A Simple Method for Assessment of the Human Acrosome Reaction of Spermatozoa Bound to the Zona Pellucida: Lack of Relationship With Ionophore A23187–Induced Acrosome Reaction."*Human Reproduction.*vol. 11, No. 3, pp. 551–557.

Mortimer, David and Lynn Fraser. 1996. "Consensus Workshop on Advanced Diagnostic Andrology Techniques: ESHRE Andrology Special Interest Group."*Human Reproduction.*vol. 11, No. 7, pp. 1463–1479.

Bagavant et al. 1997. "Immunogenicity and Contraceptive Potential of a Zona Pellucida 3 Peptide Vaccine."*Biology of Reproduction.*vol. 56, No. 3, pp. 764–770; XP–002108575.

Oehninger, Sergio et al. Mar. 1997. "Approaching the Next Millennium: How Should We Manage Andrology Diagnosis in the Intracytoplasmic Sperm Injection Era?"*Fertility and Sterility.*vol. 67, No. 3, pp. 434–436.

Oehninger, Sergio et al. Jun. 1997. "Clinical Significance of Human Sperm–Zona Pellucida Binding."*Fertility and Sterility*.vol. 67, No. 6 pp. 1121–1127.

Carver–Ward, J. A. et al. 1997. "Genetics: Comparative Flow Cytometric Analysis of the Human Sperm Acrosome Reaction Using CD46 Antibody and Lectins."*Journal of Assisted Reproduction and Genetics*.vol. 14, No. 2, pp. 111–119.

Franken, D. R. et al. 1997. "Zona Pellucida Mediated Acrosome Reaction and Sperm Morphology."*Andrologia*. vol. 29, pp. 311–317.

Kohn, F. M. et al. 1997. "Detection of Human Sperm Acrosome Reaction: Comparsion Between Methods Using Double Staining, *Pisum Sativum*Agglutinin, Concanavalin A and Transmission Electron Microscopy."*Human Reproduction*.vol. 12, No. 4, pp. 714–721.

Margalit, I. et al. 1997. "A Novel Method for Evaluating the Acrosomal Status of Mammalian Spermatozoa."*Archives of Andrology*.vol. 38, pp. 87–99.

Mortensen, Richard et al. 1997. "Selection of Transfected Mammalian Cells."*Current Protocols in Molecular Biology*.pp. 9.5.1–9.5.6.

Shalgi, R. and T. Raz. 1997. "The Role of Carbohydrate Residues in Mammalian Fertilization."*Histol Histopathol*. vol. 12, pp. 813–822.

Arkin, Shy. Feb. 20, 1998. "Protein Glycosylation."*www.bio.cam.ac.uk/~sa232/tex/MVSTIA_4–8_Shy/node13.html*. Printed Feb. 4, 1999.

Hansen, Jan. Aug. 4, 1998. "NetOGlyc 2.0 Prediction Server: Center for Biological Sequence Analysis." www.cbs.dtu.dk/services/NetOGlyc/. Printed Feb. 4, 1999.

Chuang, Alex T. and Stuart S. Howards. Nov. 1998. "Male Infertility: Evaluation and Nonsurgical Therapy."*Office Management of Urologic Problems*.vol. 25, No. 4, pp. 703–713.

Greenhouse, Stephen et al. 1998. "Insights from Model Systems: Genetic Causes of Female Infertility: Targeted Mutagenesis in Mice."*Am. J. Hum. Genet*.vol. 62, pp. 1282–1287.

Hansen, Jan E. et al. 1998. "NetOglyc: Prediction of Mucin Type O–Glycosylation Sites Based on Sequence Context and Surface Accessibility."*Glycoconjugate Journal*.vol. 15, pp. 115–130.

Henkel, R. et al. 1998. "Zona Pellucida as Physiological Trigger for the Induction of Acrosome Reaction."*Adrologia*.vol. 30, pp. 275–280.

Irvine, D. S. 1998. "Epidemiology and aetiology of male infertility."Hum. Reprod. vol. 13, No. 1, pp. 33–44.

Oehninger, S. et al. 1998. "Involvement of Selectin–Like Carbohydrate Binding Specificity in Human Gamete Interaction."*Andrologia*.vol. 30, pp. 269–274.

Jaiswal, B.S. et al. 1999. "Detection of Partial and Complete Acrosome Reaction in Human Spermatozoa: Which Inducers and Probes to Use?"*Molecular Human Reproduction*. vol. 5, No. 3, pp. 214–219.

Tsubamoto, H. et al. 1999. "Expression of recombinant human zona pellucida protein 2 and its binding capacity to spermatazoa."*Biol. Reprod*.vol. 61, pp. 1649–54.

Dean, Jurien. Jun. 24, 2000. "Maternal Effects on Folliculogenesis, Fertilization and Early Development."*Program & Abstracts: The Endocrine Society's 82nd Annual Meeting*.Oocyte Development Symposium Session.

Latif, R. and P. Graves. 2000. "Techniques in Thyroidology: Fluorescent Probes: Looking Backward and Looking Forward."*Thyroid*.vol. 10, No. 5.

Patra, Ashok K. et al. 2000. "Refolding, Structural Transition and Spermatozoa–Binding of Recombinant Bonnet Monkey (Macaca Radiata) Zona Pellucida Glycoprotein–C Expressed in *Escherichia Coli.*" *Eur. J. Biochem*.vol. 267, pp. 7075–7081.

Dong, Ke Wen et al. 2001. "Characterization of the Biologic Activties of a Recombinant Human Zona Pellucida Protein 3 Expressed in Human Ovarian Teratocarcinoma (PA–1) Cells."*Am. J. Obstet, Gynecol*.vol. 184, pp. 835–844.

Pietrobon, Elisa O. et al. Jan./Feb. 2001. "Dectection of the Mouse Acrosome Reaction by Acid Phosphtase. Comparsion With Chlortetracycline and Electron Microscopy."*Journal of Andrology*.vol. 22, No. 1, pp. 96–103.

Esterhuizen, A.D. et al. 2001. "Clinical Importance of Zona Pellucida–Induced Acrosome Reaction and Its Predictive Value for IVF."*Human Reproduction*.vol. 16, No. 1, pp. 138–144.

Zhao, Ming et al. May 2002. "Conserved Furin Cleavage Site Not Essential for Secretion and Integration of ZP3 into the Extracellular Egg Coat of Transgenic Mice."*Molecular and Cellular Biology*.vol. 22, No. 9, pp. 3111–3120.

Mar. 21, 2005. Communication from Euprean Patent Office regarding EP 02753427.0.

Kinloch, Ross A. et al. 1989. "Profile of a Mammalian Sperm Receptor Gene."*The New Biologist*.vol. 1, No. 3, pp. 232–238.

Oehninger, Sergio et al. 1992. "Male Infertility: The Impact of Assisted Reproductive Techniques."*Current Opinion in Obstetrics and Gynecology*.4; 185–196.

* cited by examiner a  p<0.05 compared to negative controls b  not significant compared to negative control

SEQUENCE LISTING

```
<160> NUMBER OF SEQ ID NOS: 7

<210> SEQ ID NO 1
<211> LENGTH: 28
<212> TYPE: DNA
<213> ORGANISM: Artificial Sequence
<220> FEATURE:
<223> OTHER INFORMATION: PCR Primers A for RT-PCR amplification of first strand of cDNA fr
      om the RNA sample of PA-1 cells stable transfected with human ZP3
      cDNA
<220> FEATURE:
<221> NAME/KEY: primer_bind
<222> LOCATION: (1)..(28)
<223> OTHER INFORMATION:

<400> SEQUENCE: 1
taggatccac catggactga gctatagg                                              28
```

```
<210> SEQ ID NO 2
<211> LENGTH: 33
<212> TYPE: DNA
<213> ORGANISM: Artificial Sequence
<220> FEATURE:
<223> OTHER INFORMATION: PCR Primers B for RT-PCR amplification of first strand of cDNA fr
      om the RNA sample of PA-1 cells stable transfected with human ZP3
      cDNA
<220> FEATURE:
<221> NAME/KEY: primer_bind
<222> LOCATION: (1)..(33)
<223> OTHER INFORMATION:

<400> SEQUENCE: 2
ttattcggaa gcagacacag ggtgggaggc agt                                33

<210> SEQ ID NO 3
<211> LENGTH: 59
<212> TYPE: DNA
<213> ORGANISM: Artificial Sequence
<220> FEATURE:
<223> OTHER INFORMATION: PCR Primers C for RT-PCR amplification of first strand of cDNA fr
      om the RNA sample of PA-1 cells stable transfected with human ZP3
      cDNA
<220> FEATURE:
<221> NAME/KEY: primer_bind
<222> LOCATION: (1)..(59)
<223> OTHER INFORMATION:

<400> SEQUENCE: 3
ttctcgagtt aatgatgatg atgatgatgt tcggaagcag acacagggtg ggaggcagt    59

<210> SEQ ID NO 4
<211> LENGTH: 28
<212> TYPE: DNA
<213> ORGANISM: Artificial Sequence
<220> FEATURE:
<223> OTHER INFORMATION: Sense primer designed based on the published sequence of hZP3 cDN
      A with additional restriction enzyme sites and histidine tail (Ch
      ambgerlin and Dean, 1990)
<220> FEATURE:
<221> NAME/KEY: primer_bind
<222> LOCATION: (1)..(28)
<223> OTHER INFORMATION:

<400> SEQUENCE: 4
taggatccac catggagtga gctatagg                                      28

<210> SEQ ID NO 5
<211> LENGTH: 61
<212> TYPE: DNA
<213> ORGANISM: Artificial Sequence
<220> FEATURE:
<223> OTHER INFORMATION: Antisense primer designed based on the published sequence of hZP3
      cDNA with additional restriction enzyme sites and histidine tail
      (Chambgerlin and Dean, 1990)
<220> FEATURE:
<221> NAME/KEY: primer_bind
<222> LOCATION: (1)..(61)
<223> OTHER INFORMATION:

<400> SEQUENCE: 5
ttctcgagtt aatgatgatg atgatgagat gttcggaagc agacacaggg tgggaggcag   60
t                                                                   61
```

```
<210> SEQ ID NO 6
<211> LENGTH: 27
<212> TYPE: DNA
<213> ORGANISM: Artificial Sequence
<220> FEATURE:
<223> OTHER INFORMATION: Sense primer designed based on the published sequence of hZP3 cDN
      A with additional restriction enzyme sites and histidine tail (Ch
      ambgerlin and Dean, 1990), located between 1 to 22 with Bam HI si
      te in the 5' end

<400> SEQUENCE: 6
taggatccat ggagctgagc tataggc                                27

<210> SEQ ID NO 7
<211> LENGTH: 59
<212> TYPE: DNA
<213> ORGANISM: Artificial Sequence
<220> FEATURE:
<223> OTHER INFORMATION: Antisense primer designed based on the published sequence of hZP3
      cDNA with additional restriction enzyme sites and histidine tail
      (Chambgerlin and Dean, 1990), located between base 1256 and 1262
<220> FEATURE:
<221> NAME/KEY: primer_bind
<222> LOCATION: (1)..(27)
<223> OTHER INFORMATION:

<400> SEQUENCE: 7
ttctcgagtt aatgatgatg atgatgatgt tcggaagcag acacagggtg ggaggcagt    59
```

HUMAN ZONA PELLUCIDA PROTEIN 3 AND USES THEREOF

This application is a continuation-in-part of U.S. application Ser. No. 09/252,828, filed Feb. 19, 1999, which claims the benefit of U.S. Provisional Application No. 60/075,079, filed Feb. 19, 1998. The content of these applications is incorporated by reference into this application.

Throughout this application, various references are referred to within parenthesis. Disclosures of these publications in their entireties are hereby incorporated by reference into this application to more fully describe the state of the art to which this invention pertains.

FIELD OF THE INVENTION

A method to determine sperm activity and a diagnostic kit for the same purpose.

BACKGROUND OF THE INVENTION

Earlier studies have led to the characterization of the protein components of the zona pellucida (ZP) from a variety of mammalian species, with the majority of the work being performed in the murine and porcine species. The reported number of discrete proteins comprising the ZP from different mammalian species varies (Dunbar et al, 1981; 1994; Timmons and Dunbar, 1988; Bleil and Wassarman, 1980). Murine studies have revealed that the ZP is composed of three sulfated glycoproteins, referred to as ZP1, ZP2 and ZP3. Extensive work in this model has resulted in the identification and isolation of the primary receptor for sperm located at the level of the zona pellucida, a glycoprotein called zona pellucida protein 3 (ZP3) (Bleil and Wassarman, 1980; Wassarman, 1990 a and b). The binding of sperm to ZP is supported by ZP3 and complementary binding protein (s) present in the sperm plasma membrane (Saling, 1989; Wassarman, 1990; Saling, 1991). Genes homologous to the ZP2 and/or ZP3 genes have been cloned for the mouse (ZP3 and ZP2), marmoset (ZP3), human (ZP3), rabbit (rc75), and marmoset (Ringuette et al., 1986; Liang et al., 1990; Kinloch et al., 1990; Chamberlin & Dean, 1990; Liang & Dean, 1993; Lee et al., 1993; Thillai-Koothan et al., 1993). Genes encoding ZP2 and ZP3 are conserved among mammals and sequences of ZP3 cDNA coding regions show extensive homology between species studied so far.

Cloning cDNAs encoding ZP3 has made the expression of recombinant ZP3 in tissue culture cell lines possible and represents the potential to obtain large amounts of recombinant ZP3. The expression of biologically active recombinant ZP3 has been reported, at least, in the mouse (Kinloch et al, 1991; Beebe et al, 1992) and human (van Duin et al, 1994; Barratt et al, 1994; Burks et al, 1995). In the mouse, some of these recombinant proteins have demonstrated partial or full biological activity in ligand-receptor or acrosome reaction assays. Expression of recombinant ZP proteins is not restricted to those of the mouse and human species. Prasad et al (1996) demonstrated that recombinant rabbit 55 kDa protein (which is thought to be the rabbit homologue of mouse ZP1) purified from a baculovirus expression system could be used to generate a polyclonal antiserum which was then employed to study the localization of the native 55 kDa protein in rabbit zona.

On the other hand, recombinant human ZP3 has been expressed using several approaches, i.e., *Escherichia coli* (Chapman and Barratt, 1996), in vitro transcription and translation systems (Whitmarsh et al, 1996), Chinese hamster ovary (CHO) cells (van Duin et al, 1994; Barratt and Hornby, 1995; Brewis et al, 1996) and in African green monkey kidney (COS) cells (Burks et al, 1995). In the human, however, full biological activity, which includes the ability to bind spermatozoa in a specific fashion and to induce the acrosome reaction, has not been fully demonstrated for such products. This is possibly due, among other reasons, to inadequate or incomplete glycosylation of the recombinant protein (Chapman and Barratt, 1997).

In the human system, production of a pure recombinant ZP3 glycoprotein in a biologically active form has been fraught with technical difficulties. Expressing recombinant ZP3 protein with in vitro transcription and translation systems and in *Escherichia coli* has shown a variable acrosome reaction-inducing activity. However, no direct or specific sperm-binding ability using homologous sperm-ZP bioassays has been reported for such non-glycosylated products. In addition, protein solubility has been a major difficulty encountered (Chapman and Barratt, 1997). The rhZP3 expressed in CHO cells has been shown to possess acrosome reaction-inducing activity. However, no data are available regarding sperm binding in validated assays (van Duin et al, 1994; Barratt and Hornby, 1995). The fact that such recombinant proteins lack full sperm binding activity points to inadequate glycosylation of the protein core by the host cells.

In our studies we have cloned and expressed the cDNA of human ZP3 by stable transfection in a human ovarian cell line (PA-1 cells). This cell line was chosen to fit the glycosylation criterion, since glycosylation is tissue- and species-specific (Varki, 1993). The PA-1 cells produce glycosylated proteins such as lactosaminoglycan-carrier glycoprotein (Fukuda et al, 1985), heparin-binding protein (Furukawa et al, 1990) and fibronectin (McIlhinney and Patel, 1983), and have been successfully used as an expression host to express other glycoproteins such as Interleukin-6 receptor (Lust et al, 1995). We purified the recombinant glycoprotein product and characterized its biological activities as sperm ligand (in competition studies using a homologous sperm-zona pellucida binding bioassay) and as physiologic inducer of the acrosome reaction (triggering exocytosis of sperm in suspension and assessing the frequency of acrosome reaction by lectin binding fluorescence). A first description of the full biological activities of this product has been reported (Dong et al, 2000). Here we have focused in the molecular biology and biochemical steps involved in cloning and expression as well as in glycoprotein purification.

The zona pellucida protein 3 (ZP3) is an essential component of the reproductive system as it functions as sperm receptor on the zona and as trigger of the acrosome reaction. To date, no recombinant human ZP3 (rhZP3) with well-documented and characterized biological activity is available. The aim of these studies was to clone and express a biologically active rhZP3 in human ovarian cells. A full-length human ZP3 cDNA was generated by RT-PCR using mRNA isolated from a human ovary. Sequencing of both strands demonstrated identical composition to the previously published cDNA sequence. An in vitro transcription and translation system revealed a protein core of 47 Kd for the product. To express the human ZP3 in vitro, the ZP3 cDNA with a six-histidine tail in its 3' end was inserted into a pcDNA vector with a CMV promoter. The expression construct was introduced into PA-1 cells by stable transfection. The purification of rhZP3 was performed using Wheat Germ Agglutinin, DEAE ion exchange and Ni-NTA affinity chromatography. Western blot analysis confirmed a molecular weight of approximately 65 Kd for the secreted glycoprotein which had a PI of 4.60±0.05. Glycosylation labeling experiments demonstrated incorporation of $^3$H-galactose by the transfected cells. The rhZP3 demonstrated specific activities as ligand and inducer of the acrosome reaction of live human sperm.

SUMMARY OF THE INVENTION

The present invention provides a method to determine sperm activity comprising the steps of: (a) contacting an appropriate concentration of human zona pellucida protein 3 with an appropriate amount of sperm under conditions permitting the formation of a complex between the human zona pellucida protein 3 and the sperm; and (b) determining the complex form.

The invention further provides A method to determine sperm activity comprising the steps of (a) contacting an appropriate concentration of human zona pellucida protein 3 with an appropriate amount of sperm under conditions permitting an acrosome reaction to occur; and (b) determining the extent of the acrosome reaction.

This invention also provides a diagnosis kit for sperm activity comprising compartments with (a) an appropriate amount of human zona pellucida protein 3 and (b) the reagents used for establishing the conditions for allowing the binding of sperm.

Furthermore, this invention provides a diagnosis kit for sperm activity comprising compartments with (a) an appropriate amount of human zona pellucida protein 3 and (b) the reagents used for establishing the conditions for allowing an acrosome reaction.

Finally, this invention provides a diagnosis kit for sperm activity comprising three (3) compartments with (a) an appropriate amount of human zona pellucida protein 3; (b) the reagents used for establishing the conditions for allowing the binding of sperm; and (c) the reagents used for establishing the conditions for allowing an acrosome reaction.

DETAILED DESCRIPTION OF THE FIGURES

FIG. 1. Western Blot Analysis of protein sample from Caov-3, Caob-4, OVCAR-3, EB2, PA-1, SK-OV-3, and SW626 which were transfected with human ZP3 cDNA.

Figure 2:
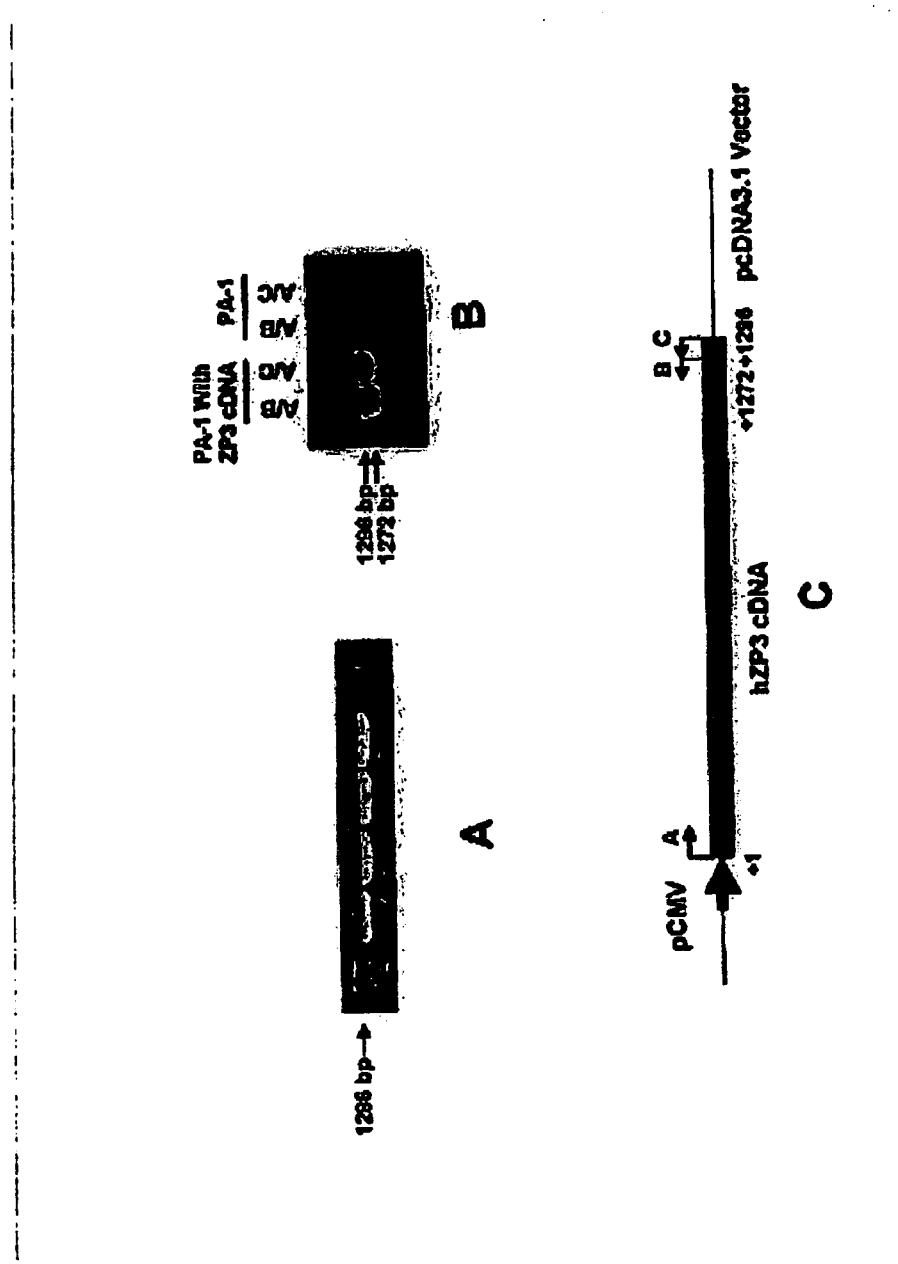

FIG. 2. Determination of expression of recombinant ZP3 in transfected PA-1 cells by RT-PCT. (A RT-PCT amplification of first strand of cDNA from the RNA sample of PA-1 cells stable transfected with human ZP3 cDNA with primers A9CH1)/B(CH2) and A/C (B1). Location of PR primers (Primer A5'-TAGGATCCACCATGGACTGAGCTATA-GG-3', SEQ ID NO: 1, Primer B5'-TTATTCGGAAGCA-GACACAGGGTGGGAGGCAGT-3', SEQ ID NO: 2, Primer C 5'-TTCTCGAGTTAATGATGATGATGATGA-TGTTCGGAAGCAGACACAGGGTGGGAGGCAGT-3') SEQ ID NO: 3

Figure 3:

FIG. 3. Protein Sample (rhZP3) from PA-1 cells stable transfected with human ZP3 cDNA and solubilized zona (hZP3) was separated by SDS-PAGE. One of the gels was stained by Coomassie Blue. The other gel was analyzed by Western Blot. The human recombinant ZP3 has an identical molecular weight as the native ZP3 from the solubilized zona.

Figure 4:
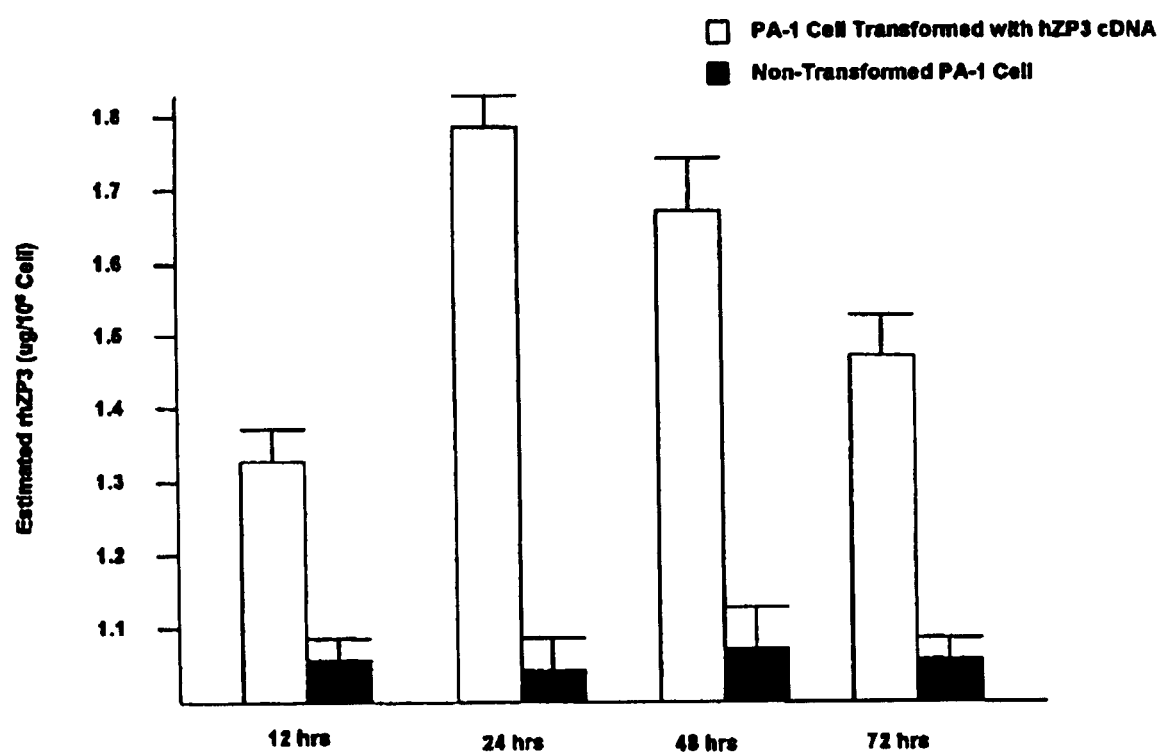

FIG. 4. Study of the expression of recombinant human ZP3 using ELISA. Results are expressed as mean+/−SEM.

Figure 5:
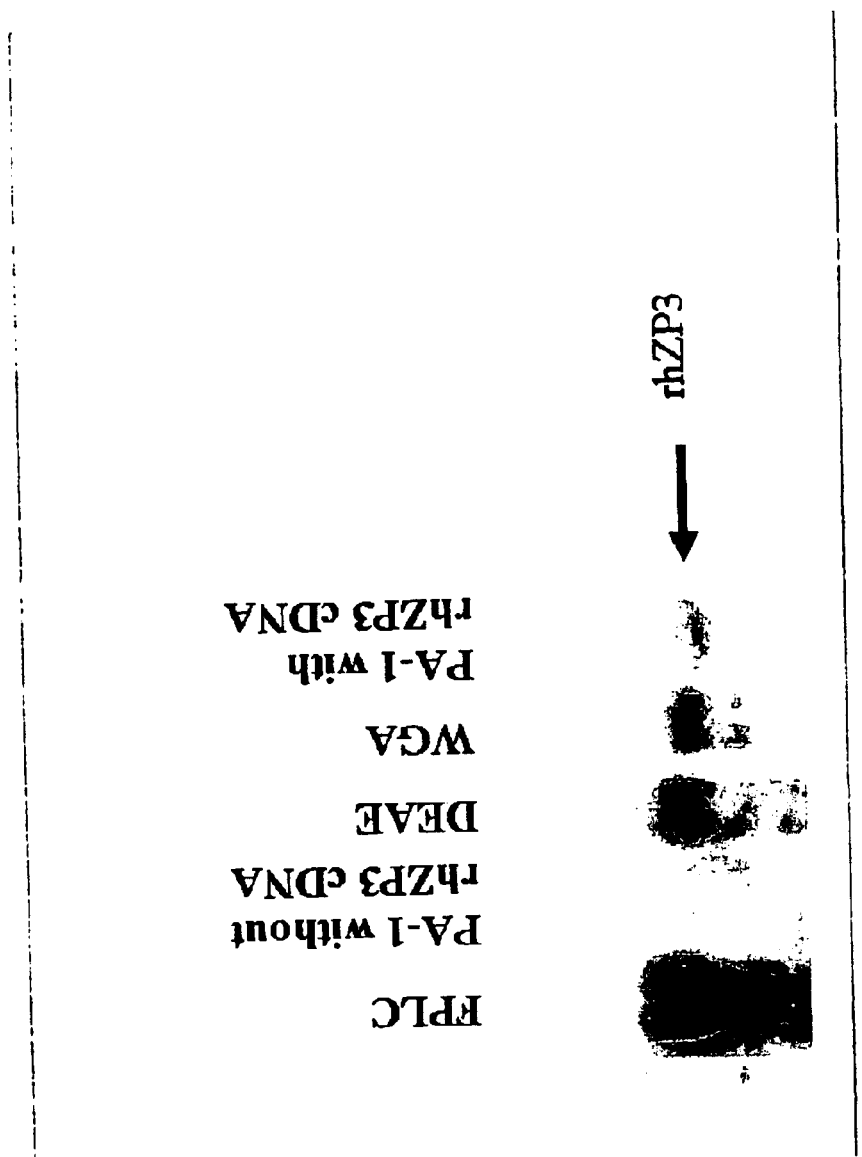

FIG. 5. Western blot analysis of recombinant human ZP3 isolated from WGA, DEAE and Ni-NTA columns. Western blot analysis of recombinant human ZP3 protein which was purified with WGA columns only(WGA), WGA and DEAE columns (DEAE) as well as WGA, DEAE and Ni-NTA columns (Ni-NTA). The protein samples purified from non-transfected PA-1 cells (PA-1 without rhZP3) was used as a negative control.

Figure 6:
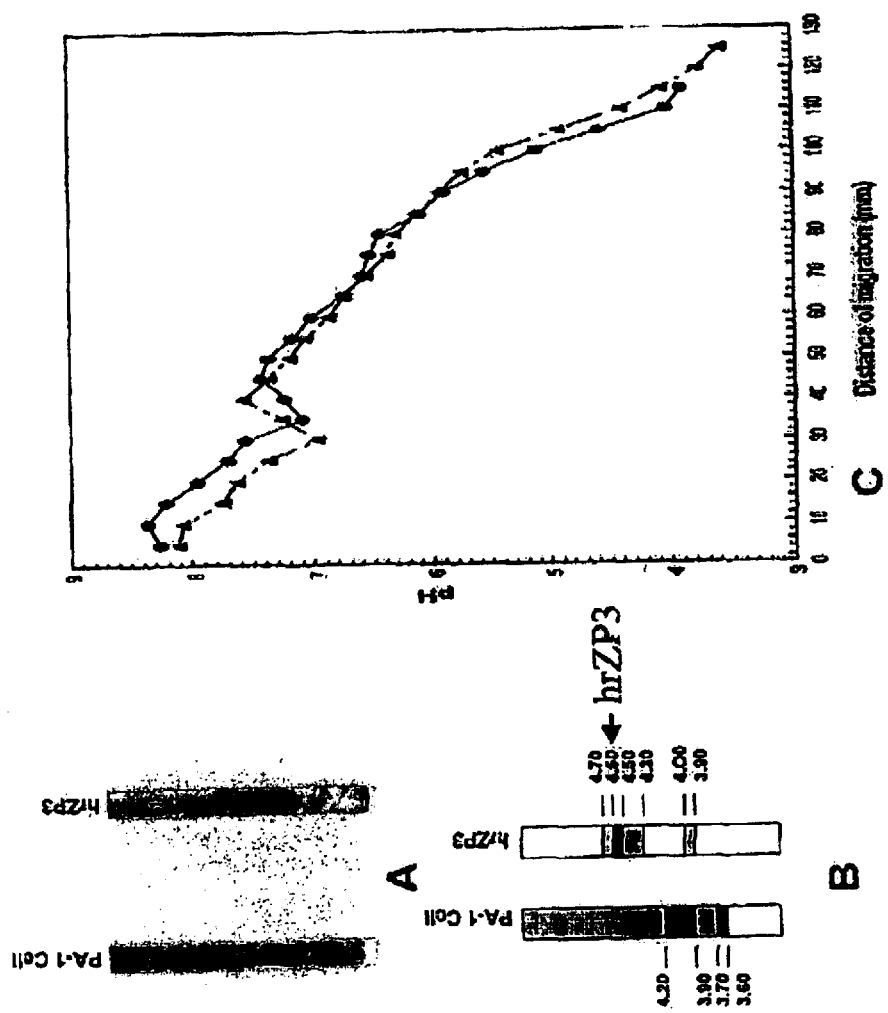

FIG. 6. Determination of isoelectric point of rhZP3 using isoelectric focusing electrophoresis. A) Photo of rhZP3 on the isoelectric focusing gel. The protein sample isolated from the non-transfected PA-1 cells was used as a negative control. B) The computer graphics represent the photo of rhZP3 on the isoelectric focusing gel (A). C) Regression analysis of isoelectric point electrophoresis.

Figure 7:
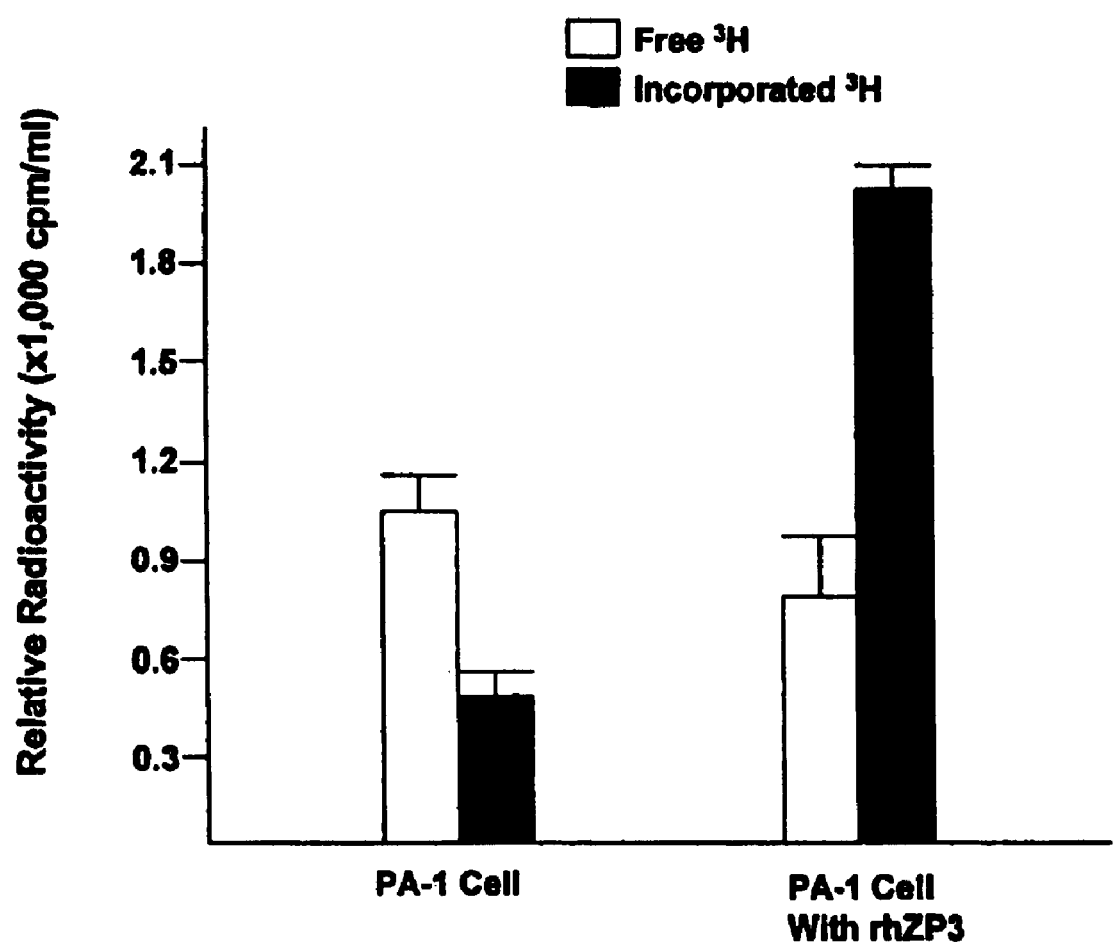

FIG. 7. $^3$H-Metabolic Labeling Study of PA-1 cells with or without transfected human ZP3 cDNA. Results are expressed as mean+/−SEM.

Figure 8:
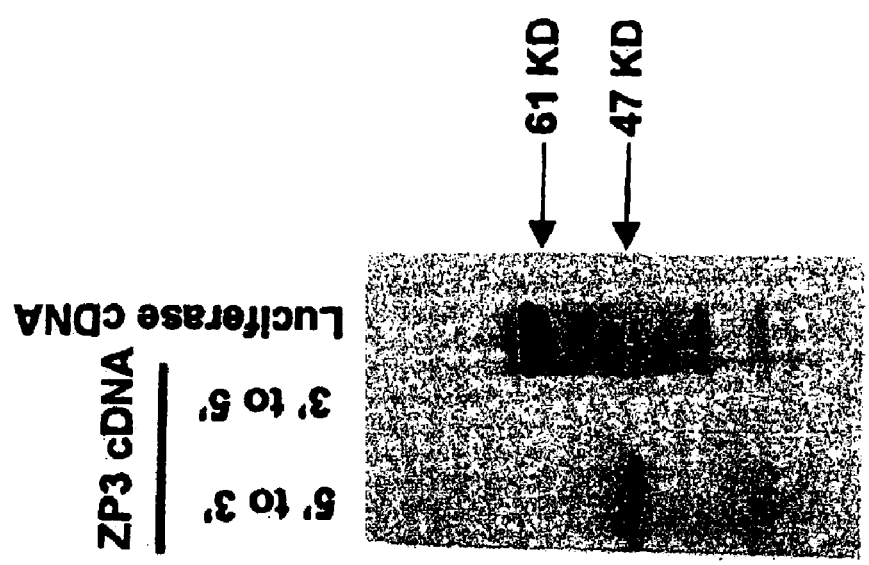

FIG. 8. In vitro transcription and translation of human ZP3 cDNA. Human ZP3 cDNA was transcribed and translated in vitro by a reticulocyte lysate system from both 5' and 3' directions. A 47-kDa protein (indicated by arrow) was observed in the cDNAs only in 5' direction. A cDNA encoding luciferase was transcribed and translated as a positive control.

Figure 9:
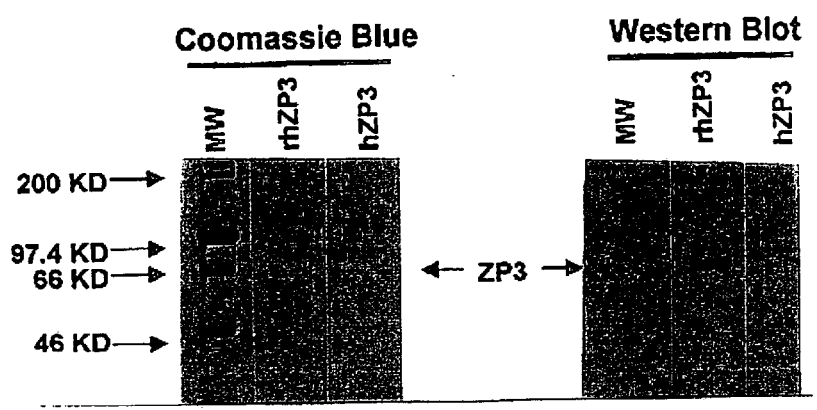

FIG. 9. A glycoprotein sample (purified by sequential WGA-DEAE-Ni-NTA chromatography) from PA-1 cells transfected with human ZP3 (rhZP3) and human solubilized zona pellucida (hZP3) were separated by SDS-PAGE. Left gel: Coomasie staining of SDS denaturing gel. Right gel: Western blot analysis. The rhZP3 has an identical molecular weight as the native ZP3 from human solubilized zona pellucida.

Figure 10:
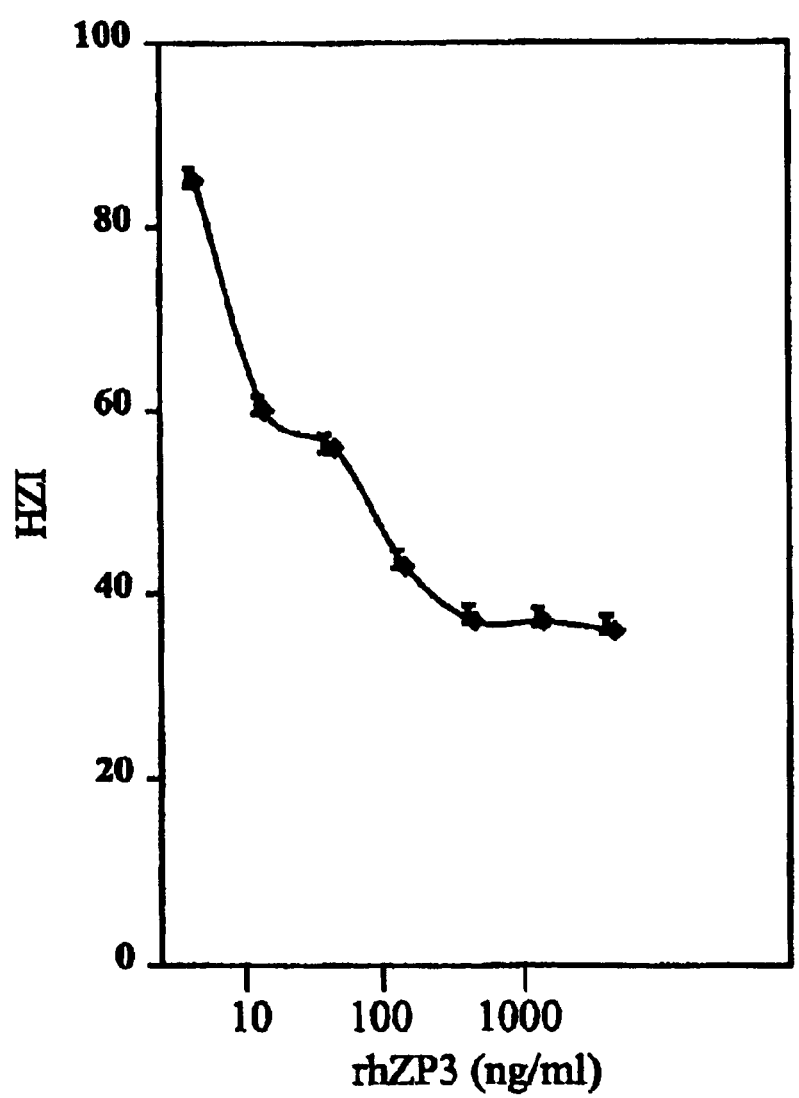

FIG. 10. Dose-dependent competitive inhibitory effect of rhZP3 on sperm-zona binding in the HZA. HZI: Hemizona index. Overall effect by ANOVA, p<0.0001.

Figure 11:
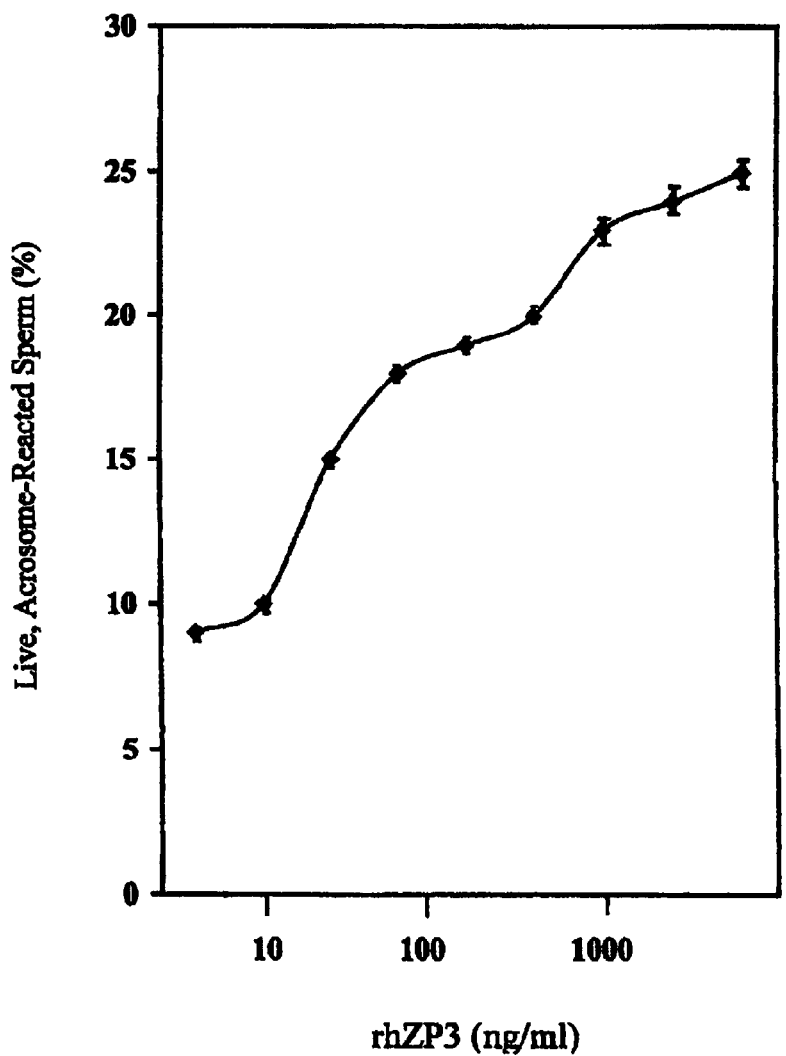

FIG. 11. Dose-dependent induction of acrosomal exocytosis of live sperm in suspension by rhZP3. Overall effect by ANOVA, p<0.001.

Figure 12:
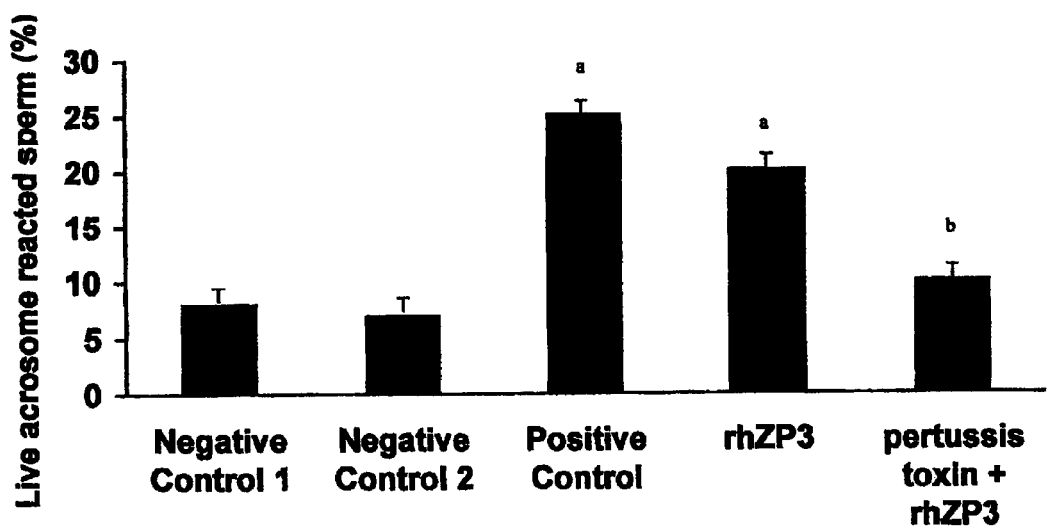

FIG. 12. The acrosome reaction-inducing activity of rhZP3 is mediated via pertussis toxin-sensitive G proteins. Negative control 1: Ham's F-10 plus HSA; negative control 2: culture medium from non-transfected PA-1 cells; positive control: calcium ionophore (5 µM); rhZP3 tested at 500 ng/mL; pertussis toxin (100 mg/mL) treated sperm then tested with rhZP3 (500 ng/mL).

DETAILED DESCRIPTION OF THE INVENTION

As used herein, "human zona pellucida protein 3" is defined as a peptide or a polypeptide comprising the binding and/or the acrosome reaction inducement domain of the native human zona pellucida protein 3.

As appreciated by an ordinary skilled artisan, the amino acid sequences of the binding and/or the acrosome reaction inducement domain may be altered without affecting the binding and/or the acrosome reaction inducement activity. Accordingly, the term "human zona pellucida protein 3" covers any variation in the amino acid sequences of the binding and/or the acrosome reaction inducement domain without affecting the biological activities of the said domains.

The present invention provides a method to determine sperm activity comprising the steps of: (a) contacting an appropriate concentration of human zona pellucida protein 3 with an appropriate amount of sperm under conditions permitting the formation of a complex between the human zona pellucida protein 3 and the sperm; and (b) determining the complex form. In an embodiment, this invention provides the above method, wherein the concentration of the human zona pellucida protein 3 is 0.01 nanograms per ml to 10,000 nanograms per ml.

In a separate embodiment, the invention provides the above method, wherein the concentration is 0.01 nanograms per ml to 5,000 nanograms per ml. In another embodiment, the invention provides the above method, wherein the concentration is 0.01 nanograms per ml to 2,500 nanograms per ml. In yet another embodiment, the invention provides the above method, wherein the concentration is 0.01 nanograms per ml to 1,000 nanograms per ml. In another embodiment, this invention provides the above method, wherein the concentration is 0.01 nanograms per ml to 500 nanograms per ml.

In a separate embodiment, this invention provides the above method, wherein the concentration is 0.01 nanograms per ml to 100 nanograms per ml. In still another embodiment, this invention provides the above method, wherein the concentration is 0.01 nanograms per ml to 30 nanograms per ml. In a separate embodiment, the invention provides the above method, wherein the human zona pellucida protein 3, or the sperm, is fixed on a matrix.

The invention further provides a method to determine sperm activity comprising the steps of (a) contacting an appropriate concentration of human zona pellucida protein 3 with an appropriate amount of sperm under conditions permitting an acrosome reaction to occur; and (b) determining the extent of the acrosome reaction.

In an embodiment, this invention provides the above method, wherein the concentration of the human zona pellucida protein 3 is 0.01 nanograms per ml to 10,000 nanograms per ml. In a separate embodiment, the invention provides the above method, wherein the concentration is 0.01 nanograms per ml to 5,000 nanograms per ml. In another embodiment, the invention provides the above method, wherein the concentration is 0.01 nanograms per ml to 2,500 nanograms per ml.

In yet another embodiment, the invention provides the above method, wherein the concentration is 0.01 nanograms per ml to 1,000 nanograms per ml. In another embodiment, this invention provides the above method, wherein the concentration is 0.01 nanograms per ml to 500 nanograms per ml. In a separate embodiment, this invention provides the above method, wherein the concentration is 0.01 nanograms per ml to 100 nanograms per ml.

In still another embodiment, this invention provides the above method, wherein the concentration is 0.01 nanograms per ml to 30 nanograms per ml. In a separate embodiment, the invention provides the above method, wherein the human zona pellucida protein 3, or the sperm, is fixed on a matrix.

This invention also provides a diagnosis kit for sperm activity comprising compartments with (a) an appropriate amount of human zona pellucida protein 3 and (b) the reagents used for establishing the conditions for allowing the binding of sperm.

Furthermore, this invention provides a diagnosis kit for sperm activity comprising compartments with (a) an appropriate amount of human zona pellucida protein 3 and (b) the reagents used for establishing the conditions for allowing an acrosome reaction.

Finally, this invention provides a diagnosis kit for sperm activity comprising three (3) compartments with (a) an appropriate amount of human zona pellucida protein 3; (b) the reagents used for establishing the conditions for allowing the binding of sperm; and (c) the reagents used for establishing the conditions for allowing an acrosome reaction.

First Series of Experiments
Materials and Methods
Isolation of Human Ovarian mRNA and Construction of cDNA for hZP3

Total RNA was isolated from the human ovary (the utilization of human tissue was approved by the Institutional Review Board of Eastern Virginia Medical School) by using the guanidium thiocyanate method (Chirgwin, et al, 1979). A pair of primers was designed based on the published sequence of hZP3 cDNA with additional restriction enzyme sites and histidine tail (Chamberlin and Dean, 1990). The sense primer was located between base 1 to 22 with Bam HI site in the 5' end (5'-TAGGATCCACCATGGAGTGAGC-TATAGG-3'). SEQ ID NO: 4. The antisense primer was located between base 1256 and 1262 (5'-TTCTCGACT-TAATGATGATGATGATGAGATGTTCGGAAGCAGA-CACAGGGTCGGAGGCAGT-3'). SEQ ID NO: 5. A SEQUENCE of Xho I restriction site and a sequence coding for six histidine residues were introduced into 5' end of this primer for the purpose of the purifying the recombinant protein as well as for subcloning. RT-PCR of the mRNA samples from human ovaries revealed a single band of approximately 1,300 bases. This PCR product was purified and inserted into a mammalian cell expression vector, pcDNA 3.1 (Invitrogen, Carlsbad, Calif.). The positive clone was sequenced and found to be identical to those of the published hZP3 (Chamberlin and Dean, 1990).

Stable-Transfection of PA-1 Cells With hZP3 cDNA

PA-1 cells (American type Culture Collection, ATCC, Rockville, Mass.) were selected for stable-transfection of hZP3 cDNA. The cells were grown in MEM medium (Sigma, St. Louis, Mo.) supplemented with 5% Fetal Bovine Serum (FBS). When the cells reached 70% confluence, the medium was changed and was transfected with 5 µg of purified hZP3 cDNA by calcium precipitation method (Sambrook et al, 1989). After 24 hours, the cells were washed three times to remove the calcium and continued to culture in the MEM medium for an additional 24 hours. Two milligrams per milliliter of neomycin were used to select the cells stable-transfected with hZP3. Approximately 10 single colonies of stable-transfected PA-1 cells were obtained. To examine whether hZP3 was expressed in these cells, RT-PCR was used with 2 primers specific to hZP3 as described above.

Cell Culture and Medium Collection

PA-1 cells were routinely cultured in MEM medium supplemented with 5% FBS in a humidified atmosphere of 5% $CO_2$ at 37° C. The medium was changed every two days. After two weeks, cell number was amplified and cells were transferred from 100 mm culture dishes to 150 mm cell culture dishes. MEM containing 50% FBS and 5% DMSO was used for freezing the transfected PA-1 cells (at −196° C. in liquid nitrogen). Since human ZP3 is a secretion protein, the culture medium from the stable transfected PA-1 cells was collected for further purification. Twenty-five dishes (150 mm) were cultured and 20 ml of medium were collected from each plate every 48 hr. The collected medium was then centrifuged at 1000 g for 10 minutes to remove cellular debris and stored at 4° C. with the addition of protease inhibitors (100 µg/ml PMSF, 2 µg/ml Leupeptin, 1 µg/ml Pepstatin and 2 mM EDTA). Glycoprotein purification was performed within a one-week period.

Sequential Affinity Chromatography

A sequential procedure combining WGA (Wheat Germ Agglutinin) (Vector laboratories, Burlingame, Calif.), DEAE ion exchange and Ni-NTA (nitrilo-tri-acetic acid, Qiagen) affinity chromatography was developed to successfully purify bioactive rhZP3. The collected medium was first passed through a 10 ml agarose-bond WGA (Vector Laboratories, Burlingame, Calif.) column at the rate of three resin volumes per hour at 4° C., to initially achieve glycoprotein separation. The glycoproteins bound to the WGA resin were eluted with WGA elution buffer (10 mM PBS, 0.15M NaCl, 0.5M N-acetyl-D-glucosamine, pH 7.4).

The eluted glycoproteins were dialyzed against DEAE cellulose binding buffer (5 mM PBS, pH 8.0) overnight at 4° C. The glycoprotein fraction isolated from the previous affinity chromatography was applied to the DEAE-Cellulose column (1×5 cm) at the flow rate of three to four resin volumes per hour. The bound protein was eluted with the same binding buffer with pH gradient from pH 8.0 to pH 3.5. Human recombinant ZP3 was eluted out between pH 6 to pH 4. The fractions containing recombinant hZP3 were dialyzed against Ni-NTA binding buffer (50 mM PBS, 300 mM NaCl, pH 8.0) overnight at 4° C. The dialyzed glycoproteins were then applied to the Ni-NTA column at a flow rate of three to four resin volumes per hour. The specific bond glycoproteins were eluted with binding buffer containing different concentrations of imidazole. The purified glycoprotein was either used immediately upon collection for testing of biological activity or stored at −20° C.

Western Blotting

The protein samples, purified by sequential affinity chromatography, were separated with 8% SDS-PAGE gels using Hoefer SE 220 minigel electrophoresis apparatus (Hoefer). An anti-ZP3 antiserum was purchased from Cocalico Biologicals, Inc. (Reamstown, Pa.). This decapeptide is a conserved epitope among different mammalian ZP3 including the human. The antiserum was produced by immunizing a rabbit with the synthetic decapeptide D-V-T-V-G-P-L-I-F-L (Hinsch et al, 1994) which was linked to keyhole limpet hemacyanin (KLH). Wet transfer of proteins from gel to hybond ECL nitrocellulose membrane (Amersham) was performed at 100 Volts for 2.5 hours at 4° C. with the transfer buffer (25 mM Tris-HCl; 192 mM glycine (Fisher); 20% methanol, pH 8.3). After transferring, the nitrocellulose membrane was blocked with blocking buffer (80% Tris-HCl buffer, pH 7.5; 15% $H_2O$; 5% BSA) at room temperature for 3 hours by gently shaking. The rabbit anti-ZP3 antiserum was used as primary antibody which was diluted at 1:1000 in solution A (80% Tris-HCl, pH 7.5; 20% BSA). Blocked nitrocellulose membrane was incubated in the primary antibody solution at room temperature for one hour with gentle shaking. The nitrocellulose membrane was washed with washing buffer A (PBS containing 0.4% Tween 20). The secondary antibody [goat anti-rabbit IgG-HRP antibody conjugate (Amersham)] was diluted by the washing buffer A at 1:2000 dilution. After washing with washing buffer, the nitrocellulose membrane was incubated in secondary antibody solution at room temperature for one hour. The membrane was washed with washing buffer B (PBS containing 0.3% Tween 20) for five minutes three times with fresh changes which was followed by washing buffer C (PBS containing 0.1% Tween 20) for five minutes three times with fresh changes of the washing buffer. The nitrocellulose membrane was exposed to the detection solution [detection reagent 1 and detection reagent 2 (1:1, v/v, Amersham)]. The membrane was placed with protein side face to film and exposed in the film cassette for 30 to 60 seconds. The film was developed with a Konica developing machine.

Metabolic Labeling Experiment

In order to label the new synthesis of glycoproteins by the PA-1 cells, a $^3H$-galactose metabolic labeling experiment was performed (Lennarz and Hart, 1994). PA-1 cells stable-transfected with or without hZP3 cDNA were cultured for 4 hours until attached to the plate surface, and then washed by 1×PBS to remove the cell-debris. A "radioactive" medium containing 250 μCi of $^3H$-galactose was added and cultured for additional 16 hours. The medium was collected and the unincorporated $^3H$-galactose was removed from the collected medium with Centriprep with a 30 kDa cut-off range (1,500×g for 30 min.). The remnant was washed three times with PBS buffer. Both the remnant and the washing solutions were collected for further analysis. The remnant was concentrated using Centricon until the final volume was 2.0 ml and passed through a WGA lectin column prepared as described previously. The WGA column was washed with ten bed volumes of WGA washing buffer, and eluted by elution buffer. Both WGA bound and non-bound fractions were collected respectively and loaded in SDS-PAGE gel with 4% stacking gel and 8% separation gel. The gel was then dried and exposed to an X-ray film.

Hemizona Assay

Hemizona assay was conducted to demonstrate the binding activity of rhZP3 to human sperm (Burkman et al, 1988; Oehninger et al, 1990, 1995). An inverted, phase-contrast microscope equipped with a micromanipulation system was routinely employed to cut the oocyte into halves to obtain matching hemizonae. Oocytes used in the experiments were obtained from surgically-removed ovarian tissue or discarded from IVF therapy under approval of the Institutional Review Board at Eastern Virginia Medical School. The hemizonae were washed in PBS to completely deplete the cytoplasm. Sperm samples were from healthy fertile donors. A swim-up procedure was applied to obtain motile sperm, which were then adjusted to 0.5 million/ml in Human Tubal Fluid (HTF) supplemented with 0.3% Human Serum Albumin (HSA) for hemizona assay. In one Petri dish, one droplet of 100 ul of sperm suspension was placed as a control. Another droplet of sperm was pre-treated with rhZP3. One hemizona was placed into the control droplet and the matching hemizona was placed in the sperm droplet treated with rhZP3. Five pairs of hemizona were used for each experiment. All dishes were incubated at 37° C., 5% $CO_2$ for 4 hours. Each hemizona was removed and rinsed 15 times in PBS, and transferred to the counting dish. The number of sperm bound to the surface of each hemizona was counted under phase microscopy. The HZI was calculated to evaluate rhZP3-binding activity (competitive inhibition) as follows: number of sperm bound for treatment/number of sperm bound for control×100.

Assessment of Acrosome Reaction

The purified rhZP3 was also applied to test its activity to induce human sperm acrosome reaction. The motile sperm obtained by swim-up procedure were allowed to capacitate in HTF/0.5% HSA for four hours at 37° C. in 5% $CO_2$ in huminified air. The motile sperm concentration used to detect acrosome reaction was set at 2 million/ml. A series of 100 ul of capacitated sperm aliquots with different inducers were prepared in Eppendorf vials and cultured in the incubator in 95% air, 5% $CO_2$, at 37° C. for 30 minutes. The test was conducted as follows: positive control: calcium ionophore A23187 (Sigma) at 5 μM; negative controls: 1) sperm culture medium alone, and 2) protein isolated from the culture media of non-transfected PA-1 cells (NT); test: rhZP3. Triple slides were made for each assay. Hoechst 33258 stain was used for determination of sperm viability. Fluorescein isothiocyanate conjugated Pisum sativum agglutinin (FITC/PSA) (Sigma) staining technique was employed to evaluate the acrosome reaction (Cross et al, 1986). Blind reading was required for evaluation and at least 100–200 cells from 5 random fields were evaluated per spot on the slide. Spermatozoa demonstrating no fluorescence over sperm head or only fluorescence at the equatorial region were considered to be acrosome-reacted. The results were expressed as percentage of acrosome-reacted spermatozoa in the total population counted (Cross, 1986).

In some experiments, Solubilized zona pellucida were used as control to test its function to induce sperm acrosome reaction. The solubilized zona pellucida were prepared according to Franken et al (1996). Ooplasma was removed using a small glass micropipette. A vigorous pipetting action would break their zona causing ooplasma to be spilled into surrounding medium. The chosen amount of zonae was transferred into an eppendorf tube and was centrifuged for 15 minutes at 300×g. Using a steromicroscope, the media were removed with pipette, making sure not to disturb zona. The final result was to remove maximum medium. A chosen volume (depending on the zona concentration needed) of 10 mM HCl was added. Under the microscopic vision, zona/HCl was pipetted up and down until all zona were dissolved. Then 10 mM NaOH of equal volume as the HCl was added and mixed well to obtain the stock zona solution.

Results

In Vitro Expression of Recombinant Human ZP3 in PA-1 Cells

A full-length human ZP3 cDNA was generated by RT-PCR using mRNA isolated from human ovarian cells. A 1,278 bp DNA fragment (full length of human ZP3 cDNA) was obtained after PCR amplification and further characterized by restriction mapping, Southern blot analysis and sequencing of both strands demonstrated identical composition to the published sequence (Chamberlin and Dean, 1990). In addition, the use of an in vitro transcription and translation system (reticulocyte lysate) demonstrated the expression of a 47 KD protein, the exact molecular weight as predicted from the DNA sequence (Dong et al, 2000).

In order to obtain high levels of expression of ZP3 in mammalian cells, the ZP3 cDNA was inserted into a pcDNA3.1 vector (Invitrogen, Carlsbad Calif.) with a CMV promoter. To insure biological activity of ZP3, the human ovarian cell was used to express the recombinant ZP3. Seven human ovarian cell lines (EB2, Caov-3, Pa-1, Caob-4, OVCAR-3, SK-OV-3, and SW626) were purchased from ATCC (Rockville, Md.) and transiently transfected with pcDNA/ZP3 expression construct. After several trials only PA-1 cells were found to exhibit high levels of expression of ZP3 with biological activity (FIG. 1). The pcDNA/ZP3 expression construct was transferred into PA-1 cells and treated with neomycin for selection of stable transfection. After three months of treatment, ten positive clones were selected. RT-PCR of the mRNA isolated from these clones, with human ZP3's specific primers, displayed high expression levels of human ZP3 (FIG. 2). ELISA analysis using the polyclonal anti-human ZP3 (anti-decapeptide antiserum) demonstrated expression of rhZP3 by the cells. One of the ten positive clones was chosen for subsequent study, as it expressed the highest levels of ZP3 with biological activity. Western Blot analysis of this protein reveals that it has an identical molecular weight, approximately 65 KD, as native human ZP3 from the solubilized zona (FIG. 3).

In order to study the expression level of hZP3 in the transfected PA-1 cell, ELISA assay was carried out. FIG. 4 shows that recombinant human ZP3 was detectable in three hours (data not shown), reaching to its peak in twenty-four hours. The recombinant human ZP3 production gradually decreased after forty-eight hours.

Isolation and Purification of Recombinant Human ZP3

Since human ZP3 is a glycoprotein, a wheat germ agglutinin (WGA) column was used to carry out the first isolation. These isolated glycoproteins were further purified using DEAE-ion exchange and Ni-NTA affinity chromatography. Approximately 3 to 5 mg of recombinant ZP3 containing glycoprotein was isolated from one liter of media (FIG. 5). Since six histdines have been added to the C-terminal of rhZP3, a Ni-NTA column was used to further purify the recombinant ZP3. Western blot analysis of this Ni-NTA mediated purification displayed a high purity of human ZP3. In parallel experiments, the protein samples were also analyzed with SDS-PAGE electrophoresis, and stained with Coomassie Blue. According to densitometer scanning analysis, rhZP3 accounted for 80% to 90% of the total purified proteins. Thus, 1 milligrams to 1.5 milligrams of rhZP3 was finally purified from one litter of culture medium (FIG. 6).

Measuring the Isoelectric Point of Recombinant Human ZP3

For further biochemical analysis, isoelectric focusing electrophoresis was performed. Approximately five microgram of recombinant ZP3 was loaded into an isoelectrophoresis tube with ampholytes (pH 3–10) in a wide range, and ampholytes (pH 4–8) in a narrow range. The same amount protein sample isolated from the PA-1 cells without transfected with hZP3 cDNA was used as a control. As shown in FIG. 6, recombinant human ZP3 had an isoelectric point of 4.60±0.05.

Determination of Glycosylation by $^3$H-Galactose Metabolic Labeling Experiment

In order to study if the new synthesis of recombinant ZP3 by the PA-1 cells is glycosylated, a $^3$H-galactose metabolic labeling experiment was carried out. FIG. 7 reveals that the PA-1 cell without stable-transfected with hZP3 has relatively low incorporation $^3$H. However, after stable-transfection with hZP3 cDNA, the relative incorporated radioactivity dramatically increased, thus indicating that a large amount of new synthesis protein was glycosylated. Electrophoresis of the product of this $^3$H-galactose metabolic labeling product has demonstrated that a great amount of $^3$H labeled protein was crowded at the regions near 65 KD (data not shown)

Testing the Sperm Binding Activity of Recombinant Human ZP3 by the Hemizona Assay Sperm culture medium (HTF/0.5% HSA) or protein isolated from medium collected from PA-1 cells which were not transfected with ZP3 cDNA (NT) was used as the internal control in each experiment. Hemizona assay results demonstrated a dramatic decrease of sperm-ZP binding when sperm were pre-incubated for 30 min with rhZP3 (approximately 60% inhibition at 30 ng/ml)). These data demonstrated that rhZP3 effects a specific and potent competitive inhibition of sperm binding to the homologous zona pellucida (Table 1).

TABLE 1

Hemizona index for testing of recombinant human ZP3 (rhZP3)

| Sperm exposed to test reagent | Sperm exposed to control conditions | HZI (Mean ± SEM) | p-value (paired t-test) |
|---|---|---|---|
| 30 ng/ml rhZP3 | HTF/0.5% HSA | 43.6 (3.3) | <0.01 |
| 30 ng/ml rhZP3 | 30 ng/ml NT | 44.5 (3.6) | <0.01 |
| 30 ng/ml NT | HTF/0.5% HSA | 94.2 (0.3) | >0.5 |

N = 5 semen donors × 5 pairs of matching hemizonae per sample

Analysis of the Ability of Recombinant Human ZP3 to Induce Sperm Aacrosome Reaction The analysis of the acrosome reaction observed in response to purified rhZP3, natural solubilized human ZP and the calcium ionophore revealed that all agonists enhanced the percentage of acrosome reacted sperm when compared to control conditions (i.e., culture medium alone or protein purified from non-transfected PA-1 cells) (Table 2). First the time course study of sperm capacitation was conducted. After different period of capacitation time, sperm were treated with rhZP3 (30 ng/ml) for thirty minutes to trigger acrosome reaction. The results indicated that there was a trend of increase in the percentage of acrosome-reacted sperm as the capacitation time prolonged (data not shown) up to 8~10 hours. In our ongoing series of experiments, 4 hour capacitation was used because at this time frame the sperm are 99% alive as compared to 86%, 82% and 66% of live sperm for 8, 12 and 24 hours of capacitation time respectively. So all experiments were performed after 4 hours of capacitation. The rhZP3 increased the percentage of acrosome-reacted by 150% from control conditions after 30 minutes of pre-incubation with sperm at 30 ng/ml. [This activity is much stronger than that reported for the CHO cell product which induced a similar percentage of acrosome reaction in human sperm following 24 hour sperm capacitation at a dose of 15–20 ng/μl (van Duin et al, 1994).]

TABLE 2

Analysis of the percentage of acrosome-reacted sperm by FITC-PSA.

| | Negative control | Non-transfected (NT, 30 ng/ml) | Calcium ionophore (5 μM) | rhZP3 (30 ng/ml) | Solubilized zona (0.5 ZP/μl) |
|---|---|---|---|---|---|
| % acrosome reacted-sperm | 7.7 (3.2) | 9.5 (2.4) | 22.5 (4.1)* | 18.3 (1.4)* | 14.8 (6.2)* |
| % sperm viability | 95.1 (2.6) | 98.0 (1.0) | 96.5 (2.0) | 96.7 (3.2) | 97.2 (2.5) |

*$P < 0.05$ compared to control conditions
Mean (± SEM), n = 29 ejaculates from 11 different donors, 3 different purification lots of rhZP3.

Discussion

ZP3 is an essential protein in the reproductive system. Because of the difficulty in obtaining human ZP3 from native sources, the mechanism(s) throughout which ZP3 is involved in human fertilization as well as the molecular structure of human ZP3 are poorly understood. Using molecular and cell biology technologies, several groups have attempted to produce biologically active recombinant human ZP3. Analysis of the current knowledge indicates that no rhZP3 with well-documented and characterized biological activities is available. Because human ZP3 has a strong hydrophobic protein backbone (Chamberlin and Dean, 1990), as well as probably large carbohydrate side chains, the glycoprotein is extremely difficult to be produced by recombinant DNA technology. Some groups have expressed ZP3 in E. Coli; this results in a low-soluble and non-glycosylated ZP3 protein (Champan and Barratt, 1996). Other groups have also attempted a cell-free translation of ZP3, also resulting in incomplete biological activity human ZP3 (Whitmarsh, et al, 1996). Other groups have used CHO cells to express ZP3 (van Duin et al, 1994). This recombinant hZP3 displayed an acrosome reaction-inducing activity only at very high levels of recombinant protein (15 to 20 μg/ml) after a long preincubation time (maximal effects observed after 18 hours). Furthermore, this recombinant protein did not demonstrate any binding activity to human sperm; therefore, it is considered that this protein only has partial biological activity.

Using RT-PCR we have generated a full length human ZP3 from the mRNA isolated from human ovary. DNA sequencing analysis of the cDNA revealed that it is identical to the published sequence (Chamberlin and Dean, 1990). In addition, the use of an in vitro transcription and translation system (reticulocyte lysate) demonstrated the expression of a 47 KD protein, the exact molecular weight as predicted from the DNA sequence (Dong et al, 2000).

Optimal glycosylation is a crucial step to produce a biologically active rhZP3. The carbohydrate side chains are important to provide solubility of the protein, and also appear to be essential for the binding activity for rhZP3. O-linked has been demonstrated to be required for the binding of mouse sperm to zona pellucida (Florman et al, 1985). Up to now there is no efficient way to modify the glycosylation of ZP3 under in vitro conditions. Therefore, selecting an expression system for the production of recombinant human ZP3 with correct glycosylation is extremely important. We believe that since glycosylation is tissue- and species-specific, expression of ZP3 cDNA in a human ovarian cell line could produce recombinant human ZP3 with full biological activity. As described in the result section, we initially tried several available human ovarian cell lines. After a long period of study, we discovered that only PA-1 cells could express the biologically active recombinant ZP3. Never before has a recombinant ZP3 protein have been shown to possess both the ability to bind to human sperm, as well as the ability to induce the acrosome reaction; yet through our studies, we have been able to generate a recombinant protein with both those abilities. Interestingly, Whitmarsh et al (1996) showed that with their in vitro transcription-translation system, their recombinant ZP3 (rZP3) supposed to be without glycosylation could have binding activity to sperm using bead coated with rZP3; they also reported that rZP3 from CHO cells could induce sperm acrosome reaction.

The biochemical studies using a cell-free translation system have demonstrated that this protein has a collect size of protein backbone (47 KD). Western blot analysis has demonstrated that this recombinant protein has approximately 65 KD, thus agreeing with the native human ZP3 (Shabanowitz et al, 1988). The result from these studies reveals that an approximately 18 KD difference between glycosylated recombinant protein and the ZP3 protein backbone may result from the glycan side chains. Furthermore, the metabolic labeling study has demonstrated that the PA-1 cells transfected with ZP3 expression vector produces a great amount of newly synthesized glycoprotein. All of these data strongly suggest that PA-1 cells can glycosylate the ZP3 protein backbone. More importantly, our rhZP3 not only can induce the acrosome reaction in capacitated human sperm, but can also function as a ligand to human sperm. Furthermore, our initial studies demonstrated that these biological activities display a dose-responsive pattern. (Dong et al, 2000)

Isoelectrical point studies have shown that the rhZP3 has PI values approximately near pH 5.60, suggesting that our recombinant ZP3 produced by the PA-1 cells may have different degrees of glycosylation. As control, we have used a protein sample that was collected from PA-1 cells not transfected with the hZP3 cDNA; these samples were purified by the sequential affinity chromatographic procedures used to purify rhZP3. This control sample displayed a different pattern (with PI values approximately near pH 5.4) from that of human recombinant ZP3; thus rejecting possibilities of contamination with other secretion proteins from PA-1 cells. Since glycosylation is a major contribution to the PI value of glycoprotein, our ZP3 shows similarities with the native ZP3 (PI value) suggesting that rhZP3 may have a similar glycoside chain pattern as native human ZP3.

Our rhZP3 demonstrated ligand activity by competitively inhibiting sperm-zona pellucida binding in the HZA. The HZA is a useful tool to examine the mechanisms of initial sperm-oocyte interaction by providing a homologous, internally controlled test that assesses the specific, irreversible and tight binding of sperm to the zona pellucida as well as the zona-induced acrosome reaction (Oehninger, 1990). To the best of our knowledge, this is the first time that a rhZP3 has been proven to competitively inhibit sperm-zona pellucida binding in a controlled fashion. Our rhZP3 also demonstrated a potent ability to induce the acrosome reaction in live spermatozoa. Here, we have proven that this effect is capacitation-dependent. Previously, we demonstrated that both ligand and acrosome reaction-inducing activities are dose-dependent, with maximal effects in the range of 30–1,000 ng/ml (Dong et al; 2000). This activity is much stronger than that reported for the CHO cell product which induced a similar percentage of acrosome reaction in human sperm following 24 hour sperm capacitation at a dose of 15–20 ng/µl (van Duin et al, 1994). The level of induction of acrosomal exocytosis was similar to the one observed for two well-known agonists used as positive controls; i.e., a calcium ionophore and solubilized human zona pellucida. The structural features of acrosome-reacted spermatozoa (assessed by transmission electronmicroscopy) also showed similarity to the acrosomal exocytotic changes observed with the control agonists (Dong et al, 2000).

In the zona pellucida, ZP3 associates with ZP2 and ZP1 to form a network structure (Wassarman, 1988). This network structure prevents aggregation of these glycoproteins. However, in solution these glycoproteins tend to aggregate together. This phenomenon has been observed in several recombinant glycoproteins, including ZP3 (Champan and Barratt, 1997). In purifying rhZP3, we have avoided this problem by obtaining a highly purified product, and testing its biological activities within a week-period while maintaining the protein at 4° C. However, we have found similar problems of aggregation of the glycoprotein as we attempted freezing the product. This problem becomes worse as larger amounts of the glycoprotein are trying to be produced. Different strategies are being looked into in order to produce and purify large amounts of biologically active rhZP3 in our laboratory.

In summary, using a human ovarian cell line, we have successfully cloned and expressed, and purified a biologically active recombinant human ZP3. This protein has a molecular weight of 65 KD, with an PI in the range of 4.6±0.05. In vitro translation by a cell-free system and $^3H$ metabolic labeling experiments revealed that our recombinant ZP3 has a large glycan side chain (approximately 18 KD). Importantly, the present data and the results of our previous studies (Dong et al, 2000) unequivocally present evidence showing that the glycoprotein has biological activity as it acts as ligand to human sperm and induces the acrosome reaction. The complete biochemical and functional characterization of this recombinant human ZP3 (rhZP3) may allow us in the future to (1) further examine the physiology of human gamete interaction including the identification of the putative receptor(s) on the surface of human sperm; (2) develop new assays to test for male infertility; and (3) investigate new contraceptive strategies.

References

Barratt, C. L. R., Whitmarsh, A., Hornby, D. P. et al. (1994) Glycosylation of human recombinant ZP3 is necessary to induce the human acrosome reaction. [Abstr. No. 033] *Hum. Reprod.*, 9 (Suppl.).

Barratt, C. L. R., and Hornby, D. P. (1995) Induction of the acrosome reaction by rhuZP3. In Frenichel, P. and Parinaud, J. (eds), *Human sperm acrosome reaction*. Colloque INSERM, John Libey Eurotext, Paris, Vol. 236, 105–122.

Beebe, S. J., Leyton, L., Burks, D. et al. (1992) Recombinant mouse ZP3 inhibits sperm binding and induces the acrosome reaction. *Dev. Biol.*, 151, 48–54.

Bleil, J. D., and Wassarman, P. M. (1980) Mammalian sperm-egg interaction: identification of a glycoprotein in mouse egg zona pellucida possessing receptor activity for sperm. *Cell*, 20:3, 873–882.

Brewis, I. A., Clayton, R., and Barratt, C. L. R. (1996) Characterization of the calcium influx and the acrosome reaction in human spermatozoa in response to recombinant ZP3. *Mol. Human Reprod.*, 2, 583–589.

Burkman, L. J., Coddington, C. C., Franken, D. R. et al. (1988) The hemizona assay (HZA): development of a diagnostic test for the binding for the binding of human spermatozoa to the human hemizona pellucida to predict fertilization potential. *Fertil. Steril.* 49, 688–697.

Burks, D. J., Carballada, R., Moore, H. D. et al. (1995) Interaction of a tyrosine kinase from human sperm with the zona pellucida at fertilization. *Science*, 269, 83–86.

Chamberlin, M. E. and Dean, J. (1990) Human homology of the mouse sperm receptor. *Proc. Natl. Acad. Sci. USA*, 87, 6014–6018.

Chapman, N. R. and Barratt, C. L. R. (1996) The role of carbohydrates in spermatozoa-zona pellucida adhesion. *Mol. Human Reprod.*, 2, 767–774.

Chapman, N. R. and Barratt, C. L. R. (1997) Sperm-zona interaction and recombinant DNA technology. *Mol. Human Reprod.*, 3, 646–650.

Chirgwin, J. M., Przybyla, A. E., MacDonald, R. J. et al. (1979) Isolation of biologically active ribonucleic acid from sources enriched in ribonuclease. *Biochem.*, 18, 5294–5299.

Cross, N. L., Morales, P., Overstreet, J. W. et al. (1986) Two simple methods for detecting acrosome-reacted human sperm. *Gamete Research*, 15, 213–226.

Dong, K. W., Chi, T. F., Juan Y. W. et al. (2000) Characterization of the biological activities of a recombinant human zona pellucida protein 3 (ZP3) expressed in human ovarian (PA-1) cells. *Am. J. Obstet. Gynecol.* (in press)

Dunbar, B. S., Avery, S., Lee, V. et al. (1994) The mammalian zona pellucida: its biochemistry, immunochemistry, molecular biology, and developmental expression. *Reprod. Fertil. Dev.*, 6, 331–347.

Dunbar, B. S., Liu, C., and Sammons, D. W. (1981) Identification of the three major proteins of procine and rabbit zona pellucida by high resolution two-dimensional gel electrophoresis: comparison with serum, follicular, fluid, and ovarian cell proteins. *Bio. Reprod.*, 24, 1111–1124.

Florman, H. M. and Wassarman, P. M. (1985) O-linked oligosaccharides of mouse egg ZP3 account for its sperm receptor activity. *Cell* 41, 313–324.

Franken, D. R., Morales, P. J. and Habenicht, U. F. (1996) Inhibition of G protein in human sperm and its influence on acrosome reaction and zona pellucida binding. *Fertil. Steril.* 66, 1009–1011.

Fukuda, M. N., Dell, A., Oates, J. E. et al. (1985) Embryonal lactosaminoglycan. The structure of branched lactosaminoglycans with novel disialosyl (sialyl alpha 2---9 sialyl) terminals isolated from PA1 human embryonal carcinoma cells. *J. Biol. Chem.*, 260, 6623–6631.

Furukawa, T., Ozawa, M., Huang, R. P. et al. (1990) A heparin binding protein whose expression increases during differentiation of embryonal carcinoma cells to parietal endoderm cells: cDNA cloning and sequence analysis. *J. Biochem.* (Tokyo), 108, 297–302.

Hinsch, K. D., Hinsch, E., Meinecke, B. et al. (1994) Identification of mouse ZP3 protein in mammalian oocytes with antisera against synthetic ZP3 peptides. *Biol. Reprod.* 51, 193–204

Kinloch, R. A., Ruiz-Seiler, B., and Wassarman, P. M. (1990) Genomic organization and polypeptide primary structure of zona pellucida glycoprotein hZP3, the hamster sperm receptor [published erratum appears in *Dev. Biol.* 1991 May; 145(1): 203]. *Dev. Biol.* 142, 414–421.

Kinloch, R. A., Ruiz-Seiler, B. and Wassarman, P. M. (1991) Genomic organization and polypeptide primary structure of zona pellucida glycoprotein hZP3, the hamster sperm receptor. *Dev. Biol.*, 145, 203–204.

Lee, V. H., Schwoebel, E., Prasad, S. et al. (1993) Identification and structural characterization of the 75-kDa rabbit zona pellucida protein. *J. Biol. Chem.* 268, 12412–12417.

Lennartz, W. J. and Hart, G. W. (1994) *Methods in Enzymology.* 230 (2), 16–32.

Liang, L. F., Chamow, S. M. and Dean, J. (1990) Oocyte-specific expression of mouse ZP-2: Developmental regulation of the zona pellucida genes. *Mol. Cell. Biol.*, 10, 1507–1515.

Liang, L. F., and Dean, J. (1993) Conservation of mammalian secondary sperm receptor genes enables the promoter of the human gene to function in mouse oocytes. *Dev. Biol.* 156, 399–408.

Lust, J. A., Jelinek, D. F., Donovan, K. A. et al. (1995) Sequence, expression and function of an mRNA encoding a soluble form of the human interleukin-6 receptor (sIL-6R). *Curr. Top. Microbiol. Immunol.* 194, 199–206.

McIlhinney, R. A. J. and Patel, S. (1983) Characterization of the fibronectin synthesized by human germ cell tumors. *Cancer Research,* 43, 1282–1288.

Oehninger, S., Acosta, A. A., and Hodgen, G. D. (1990) Antagonistic and agonistic properties of saccharide moities in the hemizona assay. *Fertil. Steril.* 55, 165–169.

Oehninger, S., Coddington, C. C., Hodgen, G. D. et al. (1995) Factors affecting fertilization: endometrial placental protein 14 reduces the capacity of human spermatozoa to bind to the human zona pellucida. *Fertil. Steril.* 67, 1121–1127.

Prasad, S. V., Wilkins, B., Skinner, S. M. et al. (1996) Evaluating zona pellucida structure and function using antibodies to rabbit 55 kDa ZP protein expressed in baculovirus expression system. *Mol. Reprod. Dev.*, 43, 519–529.

Ringuette, M. J., Sobieski, D. A., Chamow, S. M. et al. (1986) Oocyte-specific gene expression: molecular characterization of a cDNA coding for ZP3, the sperm receptor of the mouse zona pellucida. *Proc. Natl. Acad. Sci. USA,* 83:12, 4341–4345.

Saling, P. M. (1989) Mammalian sperm interaction with extracellular matrices of the egg. *Oxf Rev Reprod Biol,* 11, 339–388.

Saling, P. M. (1991) How the egg regulates sperm function during gamete interaction: facts and fantasies. *Biol. Reprod.,* 44, 246–251.

Sambrook J., Fritsch E. F., and Manatis T. (1989) Molecular cloning: a laboratory manual. ($2^{nd}$ ed) p. 16.32–16.37, Cold Spring Harbor laboratory Press.

Shabanowitz, R. B. and O'Rand M. G. (1988) Characterization of the human zona pellucida from fertilized and unfertilized eggs. *J. Reprod. Fert.* 82, 151–161.

Thillai-Koothan, P., van Duin, M., and Aitken, R. J. (1993) Cloning, sequencing and oocyte-specific expression of the marmoset sperm receptor protein, ZP3. *Zygote* 1, 93–101.

Timmons, T. M. and Dunbar, B. S. (1988) in Mathur, S. & Fredericks, C. M. (eds), *Perspectives in immunoreproduction: conception and contraception.* Hemisphere publishing Co., New York, pp 242–260 van Duin, M., Polman, J., De Breet, T. M., et al. (1994) Recombinant human zona pellucida protein ZP3 produced by Chinese hamster ovary cells induces the human sperm acrosome reaction and promotes sperm-egg fusion. *Biol. Reprod.,* 51, 607–617.

Varki, A. (1993) Biological roles of oligosaccharides: all of the theories are correct. *Glycobiology,* 3, 97–130.

Wassarman, P. M. (1988) Zona Pellucida glycoproteins. *Ann. Rev. Biochem.* 57, 415–442.

Wassarman, P. M. (1990 a) Profile of a mammalian sperm receptor. *Development,* 108, 1–17.

Wassarman, P. M. (1990 b) Regulation of mammalian fertilization by zona pellucida glycoproteins. *J. Reprod. Fertil. Suppl.,* 42, 79–87.

Whitmarsh, A. J., Woolnough, M. J., Moore, H. D. M. et al (1996) Biological activity of recombinant human ZP3 produced in vitro: potential for a sperm function test. *Mol. Human Reprod.,* 2, 911–919.

Second Series of Experiments

Objectives: To clone and express a recombinant human ZP3 (rhZP3) and to characterize its biological activities as sperm ligand and inducer of the acrosome reaction.

Study design: Human ovarian teratocarcinoma (PA-1) cells were transfected with an expression vector containing human ZP3 cDNA with a sequence coding for a six histidine tail introduced into its 3' end. Purification of the secreted glycoprotein was performed by sequential affinity (lectin and nickel-nitrilotriacetic) and ion exchange chromatography.

Results: Western blot analysis confirmed a molecular weight of approximately 65 kDa of the purified product. A cell-free translation system revealed a correct size protein backbone of 47 kDa. The rhZP3 demonstrated specific, potent and dose-dependent competitive inhibition of sperm-zona pellucida binding in vitro under hemizona assay conditions. Recombinant hZP3 also stimulated the acrosome reaction of live sperm. This effect was fast, dose- and capacitation time-dependent. Furthermore, preincubation with pertussis toxin, an inactivator of heterotrimeric G proteins blocked rhZP3-induced acrosomal exocytosis.

Conclusion: The rhZP3 expressed in PA-1 cells manifests the full spectrum of expected biological activities and, therefore, represents a valuable tool for examination of human fertilization and the design of new strategies in diagnostic male infertility and contraception.

Extensive work in the murine model has resulted in the identification and isolation of the primary receptor for sperm located at the level of the zona pellucida, a glycoprotein called zona pellucida protein 3 (ZP3) (1,2). Sperm binding to the zona pellucida is supported by the interaction of ZP3 and putative complementary binding protein(s) present in the sperm plasma membrane. In the mouse, bound sperm undergo the acrosome reaction (triggered by ZP3) and start penetration of the zona matrix (1,2). It has been proposed that GTP-binding proteins ($G_i$ class) function as a signal transducer element distal to ZP3-mediated interactions (3). ZP3-activated, heterotrimeric G proteins (pertussis toxin-sensitive) may stimulate changes in ionic conductance and/or a variety of intracellular second messenger systems resulting in acrosomal exocytosis (3).

Recently, full-length cDNA clones of ZP3 for different mammalian species have been isolated (reviewed in 4). Cloning cDNAs encoding ZP3 has made the expression of recombinant ZP3 in tissue culture cell lines possible and represents a potential option to obtain large amounts of ZP3. The expression of recombinant ZP3s has been reported, at least in the mouse and human (2,5–8). In the human, recombinant ZP3 has been expressed using several approaches; i.e., *Escherichia coli*, in vitro transcription and translation systems, Chinese hamster ovary (CHO) cells and in African green monkey kidney (COS) cells (reviewed in 6–8). However, full biological activity of a human product has not been demonstrated, which is possibly due to inadequate or incomplete glycosylation of the recombinant protein (6,7).

The production of a purified, glycosylated recombinant human ZP3 (rhZP3) in a biologically active form is fraught with technical difficulties. In vitro transcription and translation systems and expression in *Escherichia coli* have lead to the production of recombinant products showing variable acrosome reaction-inducing activity (6,7). However, no direct or specific sperm-ligand capacity using homologous sperm-zona pellucida binding bioassays has been reported for such non-glycosylated products. In addition, protein solubility has been a major difficulty encountered. The CHO cell product has been shown to possess acrosome reaction-inducing activity. However, no data are available related to sperm binding in validated assays (6–8).

Male infertility is present in 30% to 50% of childless couples and may represent the commonest single defined cause of infertility (9). Defects of sperm-zona pellucida interaction can be diagnosed in a high proportion of infertile men in the presence or absence of abnormalities of the basic sperm parameters and are associated with fertilization failure in assisted reproduction (10,11). Although sperm-zona pellucida binding and acrosome reaction bioassays have been validated in the clinical arena (10–14) the development of simpler, more standardized and universally applicable diagnostic methods are warranted. A biologically active, rhZP3 might prove to be instrumental in such an endeavor.

The objectives of these studies were: (1) to clone and express human ZP3; and (2) to characterize the biological properties of the recombinant product as sperm ligand and inducer of acrosomal exocytosis. For these purposes, we cloned and expressed the cDNA of human ZP3 by stable transfection in a human ovarian cell line (PA-1 cells). We selected this cell line since glycosylation is tissue- and species-specific and because the PA-1 cells have been successfully used as an expression host to express other glycosylated native proteins, such as lactosaminoglycan-carrier glycoprotein, heparin-binding protein and recombinant fibronectin (15). We purified the recombinant glycoprotein product and characterized its biological activities using validated bioassays. We further investigated whether rhZP3 induction of acrosomal exocytosis is mediated via signaling cascades involving activation of heterotrimeric G proteins.

Materials and Methods

These studies were approved by the Bio-safety Committee and by the Institutional Review Board at Eastern Virginia Medical School.

Isolation of human ovarian mRNA and construction of cDNA for human ZP3-Total RNA was isolated from the human ovary by using the guanidinium thiocyanate method. A pair of primers was designed based on the published sequence of hZP3 cDNA with additional restriction enzyme sites and a histidine tail (12). The sense primer is located between bases 1 to 22 with Bam HI site in the 5' end (5'-TAGGATCCATGGAGCTGAGCTATAGGC-3') SEQ ID NO: 6. The antisense primer is located between base 1256 and 1262 (5'-TTCTCGAGTTAATGATGATGATG-ATGATGTTCGAAGCAGACACAGGGTGGGAGGCA-GT-3') SEQ ID NO: 7. A sequence of Xho I restriction site and a sequence coding for six histidine residues were introduced into 5'end of this primer for the purpose of the purifying the recombinant protein as well as for subcloning. Reverse transcription-polymerase chain reaction (RT-PCR) of the mRNA samples from the human ovary revealed a single band of approximately 1,278 bp. This PCR product was further characterized by restriction mapping, Southern blotting and sequencing analysis demonstrating identical composition to be published human ZP3(16). The PCR product was inserted into a mammalian cell expression vector, pcDNA 3.1 (Invitrogen, Carlsbad, Calif.). An in vitro transcription and translation system (Reticulocyte Lysate System; Promega, Madison, Wis.) was used to determine the molecular weight of the (non-glycosylated) protein core of the recombinant ZP3.

Stable-transfection of PA-1 cells with human ZP3 cDNA-PA-1 cells (human ovarian teratocarcinoma cells, American Type Culture Collection; Rockville, Mass.) were grown in MEM (Minimal Essential Medium; Sigma Chemical Co., St. Louis, Mo.) supplemented with 5% Fetal Bovine Serum (FBS; Sigma). The cells were transfected with purified hZP3 cDNA using the calcium phosphate precipitation method. Neomycin was used to select the cells stable-transfected with human ZP3. After collection, the cell culture medium was centrifuged at 1000 g for 10 minutes to remove cellular debris and stored at 4° C. with the addition of protease inhibitors (100 µg/ml phenylmethylsulfonyl, 2 µg/ml leupeptin, 1 µg/ml pepstatin and 2 mM ethylenediaminetetraacetic acid; Sigma). The medium was maintained for no more than 5 days before glycoprotein purification and testing of biological activity.

Sequential chromatography—The collected medium was first passed through an agarose-based WGA column (Wheat Germ Agglutinin; Vector, Burlingame, Calif.) at the flow rate of three resin volumes per hour at 4° C., to initially achieve glycoprotein separation. The resin was washed with a buffer (10 mM PBS, 0.15M NaCl, pH 7.4) until the flow-through $A_{280}$ was less than 0.01. The glycoproteins bound to the WGA resin were eluted with another buffer (10 mM PBS, 0.15M NaCl, 20 mM N-acetyl-D-glucosamine, pH 7.4). The eluted glycoproteins were dialyzed against DEAE-cellulose binding buffer (5 mM PBS, pH 8.0).

The glycoprotein fraction was then applied to the DEAE-cellulose column and washed with binding buffer until the $A_{280}$ was less than 0.01. The binding protein was eluted with the same binding buffer with different pH values (from pH 7.4 to pH 3.0). Human recombinant ZP3 was eluted out between pH 4 to pH 6. This fraction was subsequently dialyzed against Ni-NTA (nitrilotriacetic acid) binding buffer (50 mM PBS, 300 mM NaCl, pH 8.0) overnight at 4° C. Before binding, the Ni-NTA resin (Qiagen, Valencia, Calif.) was equilibrated with ten bed volumes of Ni-NTA binding buffer. The dialyzed WGA-DEAE isolated glycoprotein was then applied to the Ni-NTA column at a flow rate of 3 to 4 resin volumes per hour. Afterwards, ten resin volumes of washing buffer (50 mM PBS, 300 mM NaCl, 0.1% Tween 20, 10 mM 2-mercaptoethanol, pH 8.0) were used to remove non-specific binding proteins.

The rhZP3 was eluted using a binding buffer containing various concentrations of imidazole (Sigma).

Western blotting—The isolated glycoprotein samples were separated with SDS-PAGE and transferred to a nitrocellulose membrane by electrophoresis. A rabbit polyclonal ZP3 peptide antiserum (at 2,000× dilution) produced by Dr. K. Hinsch and collaborators and kindly donated to us was used for immunologic identification of the rhZP3 (17). A synthetic ZP3 decapeptide (D-V-T-V-G-P-L-I-F-L) was used as antigen; this peptide antiserum detects ZP3 on the zona pellucida of human oocytes obtained for in vitro fertilization therapy and also on fixed ovarian tissue (18). A secondary antibody system (goat anti-rabbit IgG-Horseradish Peroxidase Antibody; Amersham Life Science, Buckinghamshire, England) was used for further identification.

Semen samples and sperm capacitation—Semen was collected by masturbation by healthy, fertile men (donors). Sperm motion parameters (% progressive motility, curvilinear and straight-line velocities, amplitude of lateral head displacement and linearity) were assessed with a computer analyzer (HTM-IVOS; Hamilton-Thorn Research, Danvers, NA). Sperm morphology was evaluated with strict criteria. The lower limits of normal parameters of samples used in the experiments were as follows: sperm concentration: $50 \times 10^6$/ml, progressive motility: 50%, and strict sperm morphology: 14% (10,11). After liquefaction, samples were washed twice in Ham's F-10 (Gibco Lab., Grand Island, N.Y.) supplemented with 0.5% human serum albumin (HSA; Irvine Sci., Santa Ana, Calif.). The final undisturbed pellet was gently over layered with 1 ml of the culture medium and the specimen was incubated for 1 hour at 37° C. in 5% $CO_2$ in humidified air to achieve separation of the highly motile sperm fractions by swim-up. Thereafter, aliquots were incubated under capacitating conditions (in Ham's F-10 plus 0.5% HSA at 37° C. in 5% $CO_2$ in humidified air) for various periods of time according to the experimental design.

Measurement of sperm-zona pellucida binding-Salt-stored, immature (prophase I) human oocytes were used in the experiments. Oocytes were desalted and microbisected into matching halves (hemizonae) using a micromanipulator (Narishige, Tokyo, Japan) following techniques published elsewhere (10, 11, 19). Control and test sperm droplets (100 μl each of a final dilution of $0.5 \times 10^6$ motile sperm/ml 1 hour post-swim-up) were incubated separately under heavy mineral oil (Sigma) with a hemizona from the same matching pair for 4 hours at 37° C. in 5% $CO_2$ in humidified air. After the co-incubation period, the hemizonae were washed to remove loosely attached sperm using a finely drawn glass pipette, and the sperm tightly bound to the outer zona surface were counted under phase microscopy (×200). The hemizona assay index (HZI) was calculated as follows: # of sperm bound for test sample/# of sperm bound for control sample×100. An HZI of 100 indicates no inhibition whereas an HZI of 0 reflects complete inhibition of binding.

Determination of the acrosome reaction—The proportion of live acrosome-reacted spermatozoa incubated under capacitating conditions was determined with the fluorescent probe fluorescein isothiocyanate-labeled Pisum Sativum Agglutinin (FITC-PSA, Sigma) after staining with a supravital stain (Hoechst 33258, Sigma) following established techniques (12,13). At least 200 sperm per sample were evaluated in duplicate at 600× magnification using an epifluorescence microscope equipped with phase-contrast optics (Optiphot; Nikon, Melville, N.Y.). Slides were coded and read in a blind fashion. Acrosome reaction was diagnosed when a total loss of the acrosomal cap was observed (bar pattern) or no immunofluorescence was seen at all (13).

A calcium ionophore agent (A23187, Sigma) tested at 5 μM and human acid solubilized zona pellucida tested at a final concentration of 4 zona/10 μl were used as positive controls (20). In further experiments, the acrosomal status was assessed by transmission electron microscopy. Spermatozoa were fixed by mixing sperm suspensions with equal volumes of 2% (v/v) glutaraldehyde (in 3 mM $CaCl_2$ and 0.1 M sodium cacodylate); thereafter, samples were dehydrated twice and prepared for thin sectioning using previously published procedures. Ultrastructural examination was performed with a transmission electron microscope (Jeol JEM-1200 EX II, Peabody, Mass.).

Experimental Design

Culture medium from non-transfected (NT) PA-1 cells grown under similar conditions and treated following the same purification procedures was used as a negative control for sperm-zona pellucida binding and acrosome reaction assays. The total protein concentration of the medium was adjusted to match the protein content of the transfected PA-1 cells containing the purified rhZP3 at each experiment.

Experiment 1: Characterization of the sperm ligand activity of rhZP3 in competitive HZA studies—The ability of the rhZP3 to competitively inhibit sperm-zona pellucida binding was assessed in dose-dependency studies using the HZA. Swim up sperm were incubated with rhZP3 (test, at a final concentration of 0, 10, 30, 100, 250, 500 or 2,000 ng/ml of protein) or in culture medium (control) for 30 min under identical conditions. After 30 min, a hemizona was added to the test sperm droplet whereas the matching hemizona from the same pair was added to the control sperm droplet. Three pairs of matching hemizonae were tested per rhZP3 concentration per semen sample in a total of three ejaculates from different donors. These studies assessed the ability of the rhZP3 to competitively inhibit sperm-zona pellucida binding.

Additional competitive HZAs were performed where the test sperm droplet (rhZP3) was assessed against control sperm droplets of culture medium from non-transfected PA-1 cells (NT). Also, competitive HZAs were carried out where the test sperm droplet (culture medium from non-transfected PA-1 cells, NT) was assayed against sperm culture medium. Three pairs of matching hemizonae were tested per dose per experiment in a total of three different ejaculates. These studies were carried out in order to examine the specificity of the effect of the rhZP3.

Experiment 2: Characterization of the acrosome reaction inducing activity of the rhZP3 in dose- and sperm capacitation-dependency studies—Motile sperm fractions from 29 ejaculates of 11 different donors were incubated under capacitating conditions for 3 hours and assayed for acrosome reaction using FITC-PSA. Following swim-up, sperm aliquots were pre-incubated for 30 minutes with rhZP3 (30 ng/ml), A23187 (positive control), culture medium from non-transfected PA-cells (NT) or sperm culture medium (negative controls). This was the initially selected dose of rhZP3 to be tested as it had proven to effect significant inhibition of sperm-zona binding in the HZA.

The dose-dependent effect of rhZP3 on acrosome reaction was examined in the swim-up fractions obtained from four different donors. The fractions were capacitated for 3 hours and exposed for 30 min to rhZP3 at final concentrations of 0, 7.5, 15, 30, 60, 120, 240, 480, 960 and 1920 ng/ml. The capacitation-dependency of the acrosome reaction-inducing activity of rhZP3 was assessed in the swim-up fractions of four ejaculates from four different donors. Capacitation times included: 0 (immediately post-swim-up), 1, 4, 8, 12 and 24 hours. After the capacitation period, rhZP3 was added to the sperm suspension at a final concentration of 30 ng/ml.

In another set of experiments, three different ejaculates were used to compare the effects of the rhZP3 (tested at 500 ng/ml) with those of solubilized zonae pellucidae and the calcium ionophore. Further, the induction of the acrosome reaction was assessed in parallel with FITC-PSA and transmission electron microscopy. The goal of these studies was to compare the morphological features of the acrosome reaction between agonists and also between the agonist-induced and basal exocytosis rates.

Experiment 3: Acrosome reaction-inducing activity of rhZP3: effect on $G_i$ proteins—Motile sperm fractions were obtained from the ejaculates of three donors and incubated under capacitating conditions. In each experiment, the test aliquot was pre-incubated with pertussis toxin (100 ng/ml final concentration) for 4 hours followed by incubation with rhZP3 (500 ng/ml). A control aliquot was incubated in culture medium alone for 4 hours and then treated with rhZP3 at the same dose. After 30 min exposure to rhZP3 or control conditions, sperm were assayed for acrosome reaction using FITC-PSA.

Results

In vitro expression and purification of rhZP3—The in vitro transcription and translation system (reticulocyte lysate) demonstrated the expression of a 47 kDa protein, the exact molecular weight as predicted from the DNA sequence of human ZP3 (FIG. 1). The purified glycoprotein from the culture medium of the transfected PA-1 cells was identified through SDS-PAGE and Western blotting; analysis revealed that the rhZP3 had an identical molecular weight (approximately 65 kDa) when compared to native human ZP3 from solubilized human zona pellucida (FIG. 2) (21, 22).

Characterization of the Biological Activities of rhZP3

Experiment 1: Inhibition of sperm-zona pellucida binding by rhZP3—Recombinant hZP3 demonstrated a significant and dose-dependent capacity to competitively inhibit binding under HZA conditions (overall effect by analysis of variance -ANOVA-, p<0.0001) (FIG. 3; data in this and following figures and tables are presented as mean±standard error of the mean). The minimally effective dose was 30 ng/ml; highest inhibition of binding (approximately 70%) was observed in the range of 500–2,000 ng/ml.

Studies addressing the specificity of the ligand activity of rhZP3 are shown in Table 3. At both 30 ng/ml and 500 ng/ml, rhZP3 produced a significant inhibition when tested against sperm culture medium or against culture medium from non-transfected PA-cells (paired t-test of rhZP3 versus control conditions, p<0.01). There were no differences between the two control conditions (sperm culture medium versus culture medium of non-transfected PA-1 cells). These results demonstrated that the effect of rhZP3 was not only dose-dependent within the nanomolar range but was also specific. Culture medium from non-transfected PA-1 cells (cultured under identical conditions and subjected to the same procedures of isolation and purification as the transfected PA-1 cells) did not produce inhibition of binding.

TABLE 3

Specificity of the inhibitory effect of rhZP3 under HZA conditions. Recombinant human ZP3 demonstrated a significant inhibitory effect on the HZI when compared to sperm culture medium alone (Ham's-HSA) and to culture medium of non-transfected PA-1 cells (NT).

| Test Reagent | versus | Control | HZI (Hemizona index) |
|---|---|---|---|
| 30 ng/mL rhZP3 | | Ham's F-10/0.5% HSA[a] | 43.6 ± 3.3 |
| 30 ng/mL rhZP3 | | 30 ng/mL NT[a] | 44.5 ± 3.6 |
| 30 ng/mL NT | | Ham's F-10-0.5% HSA[b] | 94.2 ± 0.3 |
| 500 ng/mL rhZP3 | | Ham's F-10-0.5% HSA[a] | 38.0 ± 2.7 |
| 500 ng/mL rhZP3 | | 500 ng/mL NT[a] | 41.8 ± 1.9 |
| 500 ng/mL NT | | Ham's F-10-0.5% HSA[b] | 93.4 ± 1.0 |

[a]p < 0.01 (paired t-test for test vs. control)
[b]not significant

Sperm motion parameters were not significantly different under control or treatment conditions for all of the above-mentioned experiments (data not shown). This further demonstrated that the sperm-zona binding inhibition produced by rhZP3 was not due to decreased motility parameters, given additional support to the specificity of its effect.

Experiment 2: Induction of acrosome reaction by rhZP3-Recombinant hZP3 was an effective inducer of the acrosome reaction at 30 ng/ml (the minimally effective dose for sperm-zona binding inhibition in the HZA) when compared to control conditions (sperm culture medium or culture medium from non-transfected PA-1 cells) (19±4.1% live, acrosome reacted sperm versus 9.2±3.8% and 10.2±2.7% live, acrosome reacted sperm, respectively). The magnitude of the induction of acrosome reaction was similar to that of the calcium ionophore A23187 (19.4±4.1%) (overall effect by ANOVA p<0.0001, with Bonferroni correction for multiple comparisons demonstrating differences between control conditions and rhZP3, p<0.01 and between control conditions and A23187, p<0.01).

FIG. 4 shows the dose-dependent agonistic effect of rhZP3 on the induction of the acrosome reaction (overall effect by ANOVA, p<0.0001). The minimally effective dose was 30 ng/ml; highest stimulation (approximately 210% increase from baseline conditions) was observed in the range of 500–2,000 ng/ml. There was also a significant sperm capacitation-dependency of the acrosome reaction-inducing activity of rhZP3 (ANOVA, p<0.03) with maximal stimulation observed between 8–10 hours capacitation (data not shown).

In a different set of experiments, rhZP3 (at 500 ng/ml) produced a similar induction of the acrosome reaction (28.2±5.6%) when compared to solubilized zona pellucida (23.3±6.2%) and A23187 (34.7±5.2%), all of them significantly higher (p<0.05) than negative control (sperm culture medium, 5.7±2.8%). The ultrastructural features of the acrosome reaction observed by transmission electron microscopy were similar when comparing the effect of the calcium ionophore A23187 and rhZP3. Typical features of a true acrosome reaction (i.e., broken or absent plasma and outer acrosomal membranes with various degrees of loss of acrosomal content and exposure of the inner acrosomal membrane up to the equatorial region) were observed with both treatments (not shown).

Experiment 3: Effect of rhZP3 on $G_i$ proteins—Preincubation of the motile sperm fractions with pertussis toxin (100 ng/ml) inhibited the induction of the acrosome reaction by rhZP3 (FIG. 5). Incubation with the toxin, however, did not modify the basal rate of spontaneous acrosomal exocytosis. These results demonstrate that the induction of acrosomal exocytosis by rhZP3 is mediated via a transmembrane signaling cascade involving activation of pertussis toxin-sensitive $G_i$ proteins.

Sperm motion parameters were not significantly different under control (sperm culture medium or culture medium of non-transfected PA-1 cells) or treatment (rhZP3, A23187 or pertussis toxin) conditions for experiments 2 and 3 (data not shown).

Comments

Here, we successfully cloned and expressed human ZP3 in homologous ovarian cells (PA-1) and affinity-purified a glycosylated product that demonstrated full biological activity. The rhZP3 expressed in PA-1 cells had an estimated molecular weight of approximately 65 kDa, within the published range of native human ZP3 (21,22). Furthermore, the molecular weight of the product of an in vitro transcription and translation system (reticulocyte lysate) using our recombinant vector was 47 kDa, the exact weight of the protein backbone as predicted from the DNA sequence (16). The results of our studies revealed an approximately 18 kDa difference between the rhZP3 produced by the PA-1 cells and the ZP3 protein backbone; this difference is probably due to the presence of carbohydrate side chains. Consequently, the affinity-purified rhZP3 expressed in PA-cells appears to be heavily glycosylated. A biologically active recombinant human ZP3 should present two main properties: (i) it should demonstrate specific ligand activity to capacitated spermatozoa; and (ii) it should trigger acrosomal exocytosis.

In the first experiments, our rhZP3 demonstrated ligand activity by competitively inhibiting sperm-zona pellucida binding in the HZA. The HZA is a useful tool to examine the mechanisms of initial sperm-oocyte interaction by providing a homologous, internally controlled test that assesses the specific, irreversible and tight binding of sperm to the zona pellucida as well as the zona-induced acrosome reaction (10–13,19). To the best of our knowledge, this is the first time that a rhZP3 has been proven to competitively inhibit sperm-zona pellucida binding in a controlled fashion and depicting a dose-dependent inhibition under sperm capacitating conditions. Maximal inhibition was observed in the range of 500–2000 ng/ml. This observation is consistent with the report of Franken et al. (20) who demonstrated a similar linearity of decrease of sperm-zona pellucida binding using solubilized human zona pellucida.

Glycosylation appears mandatory for ZP3-ligand function (1–3). In the mouse, ZP3-ligand activity seems to reside principally in its O-linked oligosaccharides (1–3). Evidence that the amino sugar N-acetylglucosamine is the key terminal monosaccharide involved in murine gamete interaction has also been presented (2). In the human, we demonstrated the involvement of fucosylated and sialylated complex-type glycans in sperm-zona pellucida binding (reviewed in 23,24). More recently, through the application of zona-lectin binding and chemical-enzymatic treatment studies, direct evidence was provided for the involvement of specific carbohydrate sequences (terminal sialic acid and other fucosylated structures) on human gamete interaction (24). Since the PA-1 cell glycoprotein can now be produced in large amounts, we remain hopeful that advanced methods of carbohydrate analysis will allow us to identify the saccharide epitopes responsible for sperm-zona pellucida binding in the human. In recent elegant studies, it was shown that oligosaccharides located in specific serine residues in a defined locus near the carboxyl terminus encoded by exon 7 of the mouse ZP3 gene are responsible for binding in this species (5).

Our rhZP3 also demonstrated a potent, fast dose- and capacitation-dependent ability to induce the acrosome reaction in live spermatozoa with maximal effects also observed in the range of 500 to 2,000 ng/ml. The level of induction was similar to the one observed for two well-known agonists used as positive controls; i.e., a calcium ionophore and solubilized human zona pellucida. The structural features of acrosome-reacted spermatozoa showed similarity to the acrosomal exocytotic changes observed with the control agonists. Transmission electron microscopy is still considered the "golden standard" for the assessment of true acrosome reactions and it was an important step to verify the PSA-FITC results (25).

The PA-1 cell product, therefore, was significantly more potent than rhZP3 produced in CHO cells (6–8). The CHO cell product induced acrosome reaction levels up to 30%, but only after 24 hours of incubation of the sperm with the purified rhZP3 (8). Moreover, the dose of the rhZP3 used in those experiments was 15–20 µg/ml, whereas the PA-1 cell-derived rhZP3 exhibited highest activity at 0.5–2 µg/ml, at least 10 times more potent. When an in vitro transcription and translation system was used to produce immobilized rhZP3 on agarose beads, the percentage of acrosome reaction ranged from 7 to 53% after 3 to 18 hours of sperm-beads incubation (6,7). Therefore, in terms of acrosome reaction-inducing activity, our rhZP3 appears to be more potent than the CHO cell product and comparable to the non-glycosylated product of an in vitro transcription and translation system (6–8).

We further investigated whether rhZP3 triggered acrosome reaction through a signaling cascade involving heterotrimeric G proteins (3). Pertussis toxin can cross the plasma membrane and functionally inactivate $G_i$ by ADP-ribosylating its $\propto$ subunit. Such an effect has been demonstrated using human solubilized zona pellucida (20). Here, the rhZP3-acrosome reaction inducing activity was inhibited by pre-incubation of the sperm with pertussis toxin. Such treatment did not affect the spontaneous rate of acrosomal exocytosis.

The results of our studies provide strong support for a physiological mechanism underlying the functional properties of the PA-1 cell glycoprotein product. The affinity-purified, biologically active rhZP3 expressed in the PA-1 cells represents a valuable tool to approach the study of human fertilization and the design of new diagnostic and contraceptive strategies.

References

21. Wassarman, P. M. (1990) Profile of a mammalian sperm receptor. *Development*, 108, 1–17

22. Wassarman, P. M. (1999) Mammalian fertilization: Molecular aspects of gamete adhesions, exocytosis, and fusion. *Cell* 96, 175–183

23. Kopf, G. S. (1990) Zona pellucida-mediated signal transduction in mammalian spermatozoa. *J. Reprod. Fert.* 42, 33–49

24. Harris, J., Hibler, D., Fontemot, G., Hsiu, K., Yurewicz, E., and Sacco, A. (1994) Cloning and characterization of zona pellucida genes and cDNAs from a variety of mammalian species: ZPA, ZPB and ZPC families. *DNA Sequen. Map.* 4, 361–393

25. Chen, J., Litscher, E. S., and Wassarman, P. M. (1998) Inactivation of the mouse sperm receptor, mZP3, by site-directed mutagenesis of individual serine residues located at the combing site for sperm. *Proc. Natl. Acad. Sci. U.S.A.* 95, 6193–6197

26. Chapman, N. R., and Barratt, L. R. (1996) The role of carbohydrates in spermatozoa-zona pellucida adhesion. *Mol. Hum. Reprod.* 3, 646–650

27. Whitmarsh, A. J., Woolnough, M. J., Moore, H. D. M., Hornby, D. P., and Barratt, C. L. R. (1996) Biological activity of recombinant human ZP3 produced in vitro: potential for a sperm function test. *Mol. Hum. Reprod.* 2, 911–919

28. Van Duin, M., Polman, J. E. M., De Breet, I. T. M., Van Ginneken, K., Bunschoten, H., Grootenhuis, A., Brindle, J., and Aitken, R. J. (1994) Recombinant human zona pellucida protein ZP3 *Biol. Reprod.* 51, 607–617

29. Irvine, D. S. (1998) Epidemiology and etiology of male infertility. *Hum. Reprod.* 13 (Suppl. 1), 33–44

30. Oehninger, S, Acosta, A., Veeck, L., Brzyski, R., Kruger, T. F., Muasher, S. J., and Hodgen, G. D. (1991) Recurrent failure of in vitro fertilization: Role of the hemizona assay in the sequential diagnosis of specific sperm-oocyte defects. *Am. J. Obstet. Gynecol.* 164, 1210–121

31. Oehninger, S., Mahony, M., Ozgur, K., Kolm, P., Kruger, T., and Franken, D. (1997) Clinical significance of human sperm-zona pellucida binding. *Fertil. Steril.* 67, 1121–1127

32. ESHRE Andrology Special Interest Group (1996) Advanced Diagnostic Andrology Techniques. *Hum. Reprod.* 11, 1463–1479

33. Oehninger, S., Mahony, M., Swanson, J. R., and Hodgen, G. D. (1993) The specificity of human spermatozoa/zona pellucida interaction under hemizona assay conditions. *Mol. Reprod. Dev.* 35, 59–61

34. Liu, D. Y., Lopata, A., Johnston, W. I. H., and Gordon Baker, H. W. (1988) A human sperm-zona pellucida binding test using oocytes that failed to fertilize in vitro. *Fertil. Steril.* 50, 782–788

35. Fukuda, M. N., Dell, A., Oates, J. E., and Fukuda, M. (1985) Embryonal lactosaminoglycan. The structure of branched lactosaminoglycans with novel disialosyl (sialyl alpha 2 - - - 9 sialyl) terminals isolated from PA1 human embryonal carcinoma cells. *J. Biol. Chem.,* 260, 6623–6631.

36. Chamberlin, M. E., and Dean, J. (1990) Human homology of the mouse sperm receptor. *Proc. Natl. Acad. Sci. U.S.A.* 87, 6014–6018

37. Hinsch, K. D., Hinsch, E., Meinecke, B., Topfer-Petersen, E., Pfisterer, S., and Schill, W.-B. (1994) Identification of mouse ZP3 protein in mammalian oocytes with antisera against synthetic ZP3 peptides. *Biol. Reprod.* 51, 193–204

38. oehninger, S., Hinsch, E., Pfisterer, S., Veeck, L. L., Kolm, P., Schill, W.-B., Hodgen, G. D., et al. (1996) Use of specific zona pellucida (ZP) protein 3 antiserum as a clinical marker for human ZP integrity and function. *Fertil. Steril.,* 65, 139–145.

39. Burkman, L. J., Coddington, C. C., Franken, D. R., Kruger, T., Rosenwaks, Z., and Hodgen, G. D. (1988) The hemizona assay (HZA): development of a diagnostic test for the binding of human spermatozoa to the human hemizona pellucida to predict fertilization potential. *Fertil. Steril.* 49, 688–693

40. Franken, D. R., Morales, P. J., and Habenicht, U. F. (1996) Inhibition of G protein in human sperm and its influence on acrosome reaction and zona pellucida binding. *Fertil. Steril.* 66, 1009–1011

41. Shabanowitz, R. B., O'Rand, M. G. (1988) Characterization of the human zona pellucida from fertilized and unfertilized eggs. *J. Reprod. Fertil.,* 82, 151–161.

42. Bercegeay, S., Jean, M., and Barriere, P. (1995) Composition of human zona pellucida as revealed by SDS-PAGE after silver staining. *Mol. Reprod. Dev.,* 41, 355–259.

43. Oehninger, S., Patankar, M., Seppala, M., and Clark, G. F. (1998) Involvement of selectin-like carbohydrate binding specificity in human gamete interaction. *Andrologia,* 30, 269–274

44. Ozgur, K., Patankar, M. S., Oehninger, S., and Clark, G. F. (1998) Direct evidence for the involvement of carbohydrate sequences in human sperm-zona pellucida binding. *Mol. Hum. Reprod.* 4, 318–324

45. Kohn, E. M., Mack, S. R., Schill, W. B., and Zaneveld, L. J. D. (1997) Detection of human sperm acrosome reaction: comparison between methods using double staining, Pisum Sativum agglutinin, concanavalin A and transmission electron microscopy. *Hum. Reprod.* 12, 714–721

---

What is claimed is:

1. A method to determine human sperm binding activity with human ova, comprising the steps of:
   (a) contacting glycosylated recombinant human zona pellucida protein 3, expressed from a PA-1 human ovarian cell line, with an appropriate amount of human sperm under conditions permitting the formation of a complex between the glycosylated human zona pellucida protein 3 and the sperm; and
   (b) determining the complex formed from step (a) as a measure of sperm binding activity with the human ova.

2. The method of claim 1, wherein the concentration of the human zona pellucida protein 3 is 0.01 nanograms per ml to 10,000 nanograms per ml.

3. The method of claim 1, wherein the concentration is 0.01 nanograms per ml to 5,000 nanograms per ml.

4. The method of claim 1, wherein the concentration is 0.01 nanograms per ml to 2,500 nanograms per ml.

5. The method of claim 1, wherein the concentration is 0.01 nanograms per ml to 1,000 nanograms per ml.

6. The method of claim 1, wherein the concentration is 0.01 nanograms per ml to 500 nanograms per ml.

7. The method of claim 1, wherein the concentration is 0.01 nanograms per ml to 100 nanograms per ml.

8. The method of claim 1, wherein the concentration is 0.01 nanograms per ml to 30 nanograms per ml.

9. The method of claim 1, wherein the human zona pellucida protein 3, or the sperm, is fixed on a matrix.

10. A diagnosis kit for sperm binding activity comprising compartments with (a) glycosylated recombinant human zona pellucida protein 3, expressed from a PA-1 human ovarian cell line, and (b) one or more reagents selected from the group consisting of binding buffer, Ni-NTA resin, washing buffer, and a calcium ionophore control.

* * * * *